United States Patent
Bitan et al.

(10) Patent No.: US 12,076,330 B2
(45) Date of Patent: Sep. 3, 2024

(54) INHIBITION OF LIPOFUSCIN AGGREGATION BY MOLECULAR TWEEZERS

(71) Applicants: The Regents of the University of California, Oakland, CA (US); FONDAZIONE TELETHON ETS, Rome (IT)

(72) Inventors: Gal Bitan, Los Angeles, CA (US); Alessandro Fraldi, Rome (IT); Alberto Auricchio, Rome (IT); Antonio Monaco, Rome (IT)

(73) Assignees: The Regents of the University of California, Oakland, CA (US); FONDAZIONE TELETHON ETS, Rome (IT)

( * ) Notice: Subject to any disclaimer, the term of this patent is extended or adjusted under 35 U.S.C. 154(b) by 200 days.

(21) Appl. No.: 17/050,401

(22) PCT Filed: Apr. 25, 2019

(86) PCT No.: PCT/US2019/029221
§ 371 (c)(1),
(2) Date: Oct. 23, 2020

(87) PCT Pub. No.: WO2020/036656
PCT Pub. Date: Feb. 20, 2020

(65) Prior Publication Data
US 2021/0069217 A1    Mar. 11, 2021

Related U.S. Application Data

(60) Provisional application No. 62/663,948, filed on Apr. 27, 2018.

(51) Int. Cl.
*A61K 31/6615*    (2006.01)

(52) U.S. Cl.
CPC ............... *A61K 31/6615* (2013.01)

(58) Field of Classification Search
CPC ...... A61K 31/6615; A61P 25/28; A61P 27/02; A61P 25/00; A61P 31/12; A61P 31/14; A61P 31/18; C07F 9/12; C07F 9/4084
See application file for complete search history.

(56) References Cited

U.S. PATENT DOCUMENTS

| | | | |
|---|---|---|---|
| 10,918,657 B2 | 2/2021 | Morgan et al. |
| 2011/0237538 A1 | 9/2011 | De Moor et al. |
| 2012/0108548 A1 | 5/2012 | Bitan et al. |
| 2015/0057320 A1 | 2/2015 | Petrukhin |
| 2015/0202222 A1 | 7/2015 | Morgan et al. |
| 2016/0038448 A1 | 2/2016 | Raleigh et al. |
| 2018/0306813 A1 | 10/2018 | Dobson et al. |
| 2020/0164021 A1 | 5/2020 | Kopke et al. |
| 2021/0052611 A1 | 2/2021 | Bitan et al. |
| 2021/0122771 A1 | 4/2021 | Bitan et al. |
| 2021/0137861 A1 | 5/2021 | Kopke |

FOREIGN PATENT DOCUMENTS

| | | | | |
|---|---|---|---|---|
| EP | 3112466 A1 * | 1/2017 | ......... | A61K 31/7105 |
| WO | WO-2006056182 A1 | 6/2006 | | |
| WO | WO-2010015816 A2 | 2/2010 | | |
| WO | WO-2010102248 A2 | 9/2010 | | |
| WO | WO-2010135004 A1 * | 11/2010 | ............. | A61K 38/44 |
| WO | WO-2020006489 A1 | 1/2020 | | |
| WO | WO-2020023094 A2 | 1/2020 | | |
| WO | WO-2020036656 A2 | 2/2020 | | |

OTHER PUBLICATIONS

Ratnayaka et al. (Eye, 29, 1013-26, 2015) (Year: 2015).*
Attar, A. et al., "Disrupting Self-Assembly and Toxicity of Amyloidogenic Protein Oligomers by "Molecular Tweezers"—from the Test Tube to Animal Models", Current Pharmaceutical Design, 2014, vol. 20, No. 15, pp. 2469-2483.
Attar, A. et al., "Protection of primary neurons and mouse brain from Alzheimer's pathology by molecular tweezers", Brain, Dec. 2012, vol. 135, No. 12, pp. 3735-3748.
Biase, D.D. et al., "Amyloid Precursor Protein, Lipofuscin Accumulation and Expression of Autophagy Markers in Aged Bovine Brain", BMC Veterinary Research, Apr. 13, 2017, vol. 13, No. 102, 9 pages.
Boland, B. et al., "Autophagy Induction and Autophagosome Clearance in Neurons: Relationship to Autophagic Pathology in Alzheimer's Disease", Journal of Neuroscience, Jul. 2, 2008, vol. 28, No. 27, pp. 6926-6937.
Boyer, N.P. et al., "Lipofuscin and N-Retinylidene-N-Retinylethanolamine (A2E) Accumulate in Retinal Pigment Epithelium in Absence of Light Exposure: Their Origin is 11-cis-retinal", Journal of Biological Chemistry, Jun. 22, 2012, vol. 287, No. 26, pp. 22276-22286.
Cai, S. et al., "EGCG Inhibited Lipofuscin Formation Based on Intercepting Amyloidogenic BSheet-Rich Structure Conversion", PLoS ONE, 2016, vol. 11, No. 3, e0152064, 13 pages.
Ciechanover, A. et al., "Degradation of Misfolded Proteins in Neurodegenerative Diseases: Therapeutic Targets and Strategies", Experimental & Molecular Medicine, 2015, vol. 47, No. 3, e147, 16 pages.
Extended European Search Report dated Dec. 20, 2021, in Application No. EP19850534.9.
Extended European Search Report dated Jan. 27, 2022, in Application No. EP19841367.6.

(Continued)

*Primary Examiner* — Umamaheswari Ramachandran
(74) *Attorney, Agent, or Firm* — Foley Hoag LLP; David P. Halstead; Hilary Dorr Lang

(57) ABSTRACT

In various embodiments methods for the treatment and/or prophylaxis of lipofuscin-related disorders are provided. In certain embodiments the methods involve administration of an effective amount of a molecular tweezers to a subject in need thereof.

4 Claims, 3 Drawing Sheets

(56) References Cited

OTHER PUBLICATIONS

Hohn, A. et al., "Lipofuscin: Formation, Effects and Role of Macroautophagy", Redox Biology, Jan. 19, 2013, vol. 1, No. 1, pp. 140-144.
Iannuzzi, C. et al., "The Effect of Glycosaminoglycans (GAGs) on Amyloid Aggregation and Toxicity", Molecules, Feb. 2015, vol. 20, No. 2, pp. 2510-2528.
International Preliminary Report on Patentability dated Oct. 27, 2020, in PCT Application No. PCT/US2019/029221.
International Preliminary Report on Patentability dated Oct. 27, 2020, in PCT Application No. PCT/US2019/029222.
International Search Report and Written Opinion dated Feb. 14, 2020 in PCT Application No. PCT/US2019/029222.
International Search Report and Written Opinion dated Jan. 30, 2020 in PCT Application No. PCT/US2019/029221.
Klionsky, D.J. et al., "Guidelines for the Use and Interpretation of Assays for Monitoring Autophagy (3rd edition)", Autophagy, 2016, vol. 12, No. 1, pp. 1-222.
Kovács, G. et al., "Involvement of the Endosomal-Lysosomal System Correlates With Regional Pathology in Creutzfeldt-Jakob Disease", Jul. 1, 2007, Journal of Neuropathology and Experimental Neurology, vol. 66, No. 7, pp. 628-636.
Lau, A.A. et al., "Open Field Locomotor Activity and Anxiety-related Behaviors in Mucopolysaccharidosis Type IIIA Mice", Behavioural Brain Research, Aug. 2008, vol. 191, No. 1, pp. 130-136.
Lie, P. et al., "Lysosome Trafficking and Signaling in Health and Neurodegenerative Diseases", Neurobiology of Disease, Feb. 2019, vol. 122, pp. 94-105. [HHS Public Access—Author manuscript—28 pages].
Maday, S. et al., "Autophagosomes Initiate Distally and Mature During Transport Toward the Cell Soma in Primary Neurons", Journal of Cell Biology, Feb. 20, 2012, vol. 196, No. 4, pp. 407-417.
Petrukhin, K., "Pharmacological Inhibition of Lipofuscin Accumulation in the Retina as a Therapeutic Strategy for Dry AMD Treatment", Drug Discovery Today Therapeutic Strategies, 2013, vol. 10, No. 1, pp. e11-e20.
Prabhudesai, S. et al., "A Novel "Molecular Tweezer" Inhibitor of α-Synuclein Neurotoxicity in Vitro and in Vivo", Neurotherapeutics, Apr. 2012, vol. 9, No. 2, pp. 464-476.
Pu, J. et al., "Mechanisms and Functions of Lysosome Positioning", Journal of Cell Science, Dec. 1, 2016, vol. 129, No. 23, pp. 4329-4339.
Rahimi, F. et al., "Structure-Function Relationships of Pre-Fibrillar Protein Assemblies in Alzheimer's Disease and Related Disorders", Current Alzheimer Research, Jun. 2008, vol. 5, No. 3, pp. 319-341. [NIH Public Access—Author Manuscript—43 pages].
Richter, F. et al., "A Molecular Tweezer Ameliorates Motor Deficits in Mice Overexpressing α-Synuclein" Neurotherapeutics, Oct. 2017, vol. 14, No. 4, pp. 1107-1119.
Sambri, I. et al., "Lysosomal Dysfunction Disrupts Presynaptic Maintenance and Restoration of Presynaptic Function Prevents Neurodegeneration in Lysosomal Storage Diseases", EMBO Molecular Medicine, Jan. 2017, vol. 9, No. 1, pp. 112-132.
Schrader, T. et al., "Molecular Tweezers for Lysine and Arginine—Powerful Inhibitors of Pathologic Protein Aggregation", Chemical Communications, Oct. 15, 2016, vol. 52, No. 76, pp. 11318-11334.
Serpell, L.C., "Alzheimer's Amyloid Fibrils: Structure and Assembly", Biochimica et Biophysica Acta, Jul. 26, 2000, vol. 1502, No. 1, pp. 16-30.
Settembre, C. et al., "A Block of Autophagy in Lysosomal Storage Disorders", Human Molecular Genetics, Jan. 1, 2008, vol. 17, No. 1, pp. 119-129.
Sinha, S. et al., "Lysine-Specific Molecular Tweezers are Broad-Spectrum Inhibitors of Assembly and Toxicity of Amyloid Proteins", Journal of the American Chemical Society, Oct. 26, 2011, vol. 133, No. 42, pp. 16958-16969, Retrieved from the Internet [URL: https://pubs.acs.org/doi/pdf/10.1021/ja206279b].
Sorrentino, N.C. et al., "A Highly Secreted Sulphamidase Engineered to Cross the Blood-brain Barrier Corrects Brain Lesions of Mice With Mucopolysaccharidoses Type IIIA", EMBO Molecular Medicine, May 2013, vol. 5, No. 5, pp. 675-690.
Terman, A. et al., "Lipofuscin", International Journal of Biochemistry and Cell Biology, Aug. 2004, vol. 36, pp. 1400-1404.
Uchida, K., "Lipofuscin-like Fluorophores Originated From Malondialdehyde", Free Radical Research, Dec. 2006, vol. 40, No. 12, pp. 1335-1338.
Whyte, L.S. et al., "Endo-lysosomal and Autophagic Dysfunction: a Driving Factor in Alzheimer's Disease", Journal of Neurochemistry, Mar. 2017, vol. 140, No. 5, pp. 703-717.
Wikipedia, "lipofuscin", Dec. 12, 2017, retrieved on Jan. 2, 2020 https://en.wikipedia.org/w/index.php?title=Lipofuscinoldid=815019571.
Wilkinson, F.L. et al., "Neuropathology in Mouse Models of Mucopolysaccharidosis Type I, IIIA and IIIB", PloS one, 2012, vol. 7, No. 4, e35787, 18 pages.
Acharya, S., et al., "Molecular Basis for Preventing α-Synuclein Aggregation by a Molecular Tweezer", Journal of Biological Chemistry, 2014, vol. 289, pp. 10727-10737.
Aoyagi-Scharber., et al., "Clearance of Heparan Sulfate and Attenuation of CNS Pathology by Intracerebroventricular BMN 250 in Sanfilippo Type B Mice," Molecular Therapy. Methods & Clinical Development, 2017, vol. 6, pp. 43-53.
Attar, A., et al., "Safety and Pharmacological characterization of the Molecular Tweezer CLR01, BMC Pharmacol," Toxicol, 2014, vol. 15, No. 23, DOI: 10.1186/2050-6511-15-23.
Attar, A., et al., "Modulators of Amyloid Protein Aggregation and Toxicity: EGCG and CLR01", Translational neuroscience, 2013, vol. 4, pp. 385-409.
Brunk, T., et al., "Lipofuscin: Mechanisms of Age-related Accumulation and Influence on Cell Function," Free Radical Biology & Medicine, 2002, vol. 33(5), pp. 611-619.
Dutt, S. et al., "Linker Effects on Amino Acid and Peptide Recognition by Molecular Tweezers : Recognition by Molecular Tweezers", European Journal of Organic Chemistry, Dec. 1, 2013, vol. 2013, No. 34, pp. 7705-7714.
Dutt, S., "Molecular Tweezers with Additional Binding Sites Against Protein Aggregation", Dissertation, Jan. 1, 2012, pp. 1-227.
European Office Action dated Oct. 11, 2022 for EP Application No. EP19824953.4.
Extended European Search Report dated Feb. 3, 2022 in Application No. EP19824953.4.
Ferreira, N., et al., "Molecular Tweezers Targeting Transthyretin Amyloidosis", Neurotherapeutics, 2014, vol. 11, pp. 450-461.
Fogerson, S.M., et al., "Reducing Synuclein Accumulation After Spinal Cord Injury Improves Neuronalsurvival and Axon Regeneration", Experimental Neurology, 2016, vol. 278, pp. 105-115.
Fokkens, M., et al., "A Molecular Tweezer for Lysine and Arginine", Journal of the American Chemical Society, Oct. 19, 2005, vol. 127, Issue 41, pp. 14415-14421.
Fradinger, E.A., "C-Terminal Peptides Coassemble into Aβ42 Oligomers and Protect Neurons Against Aβ42-Induced Neurotoxicity", Proceedings of the National Academy of Sciences of the United States of America, 2008, vol. 105, No. 37, pp. 14175-14180.
Heid, C., "Molekulare Pinzetten Zur Proteinoberflachenerkennung", Dissertation, Feb. 1, 2018, pp. 1-371.
Her, C., et al., "Real-Time Enzyme Kinetics by Quantitative NMR Spectroscopy and Determination of the Michaelis-Menten Constant Using the Lambert-W Function", Journal of Chemical Education, 2015, vol. 92, No. 11, pp. 1943-1948.
Herzog, G., et al., "The Lys-Specific Molecular Tweezer, CLR01, Modulates Aggregation of Mutant p53 DNA Binding Domain and Inhibitsits Toxicity", Biochemistry, 2015, vol. 54, pp. 3729-3738.
International Preliminary Report on Patentability dated Jan. 7, 2021 in PCT Application No. PCT/US2019/039943.
International Search Report and Written Opinion dated Aug. 30, 2019 in PCT Application No. PCT/US2019/039943.
JP Office Action dated Apr. 17, 2023 in Application No. JP2020-560381 with English translation.
JP Office Action dated Apr. 17, 2023 in Application No. JP2020-560382 with English translation.

(56) References Cited

OTHER PUBLICATIONS

Liu, J.B., et al., "Silver-Mediated Oxidative Trifluoromethylation of Phenols: Direct Synthesis of Aryl Trifluoromethyl Ethers", Angewandte Chemie International Edition, 2015, vol. 54, No. 40, pp. 11839-11842.

Lopes, D.H.J., et al., "Molecular Tweezers Inhibit Isletamyloid Polypeptide Assembly and Toxicity by a New Mechanism", ACS Chemical Biology, 2015, vol. 10, pp. 1555-1569.

Lulla, A., et al., "Neurotoxicity of the Parkinson's Disease-Associated Pesticide Ziram isSynuclein-Dependent in Zebrafish Embryos", Environmental Health Perspectives, 2016, vol. 124, pp. 1766-1775.

Lump, E., et al., "A Molecular Tweezer Antagonizes Seminal Amyloids and HIV Infection," eLife, Aug. 18, 2015, 4:e05397, pp. 1-33.

Malik, R., et al., "Using Molecular tweezers to Remodel Abnormal Protein Self-assembly and Inhibit the Toxicity of Amyloidogenic Proteins", Methods in Molecular Biology, 2018, vol. 1777, pp. 369-386.

Malishev, R., et al., "Toxicity Inhibitors Protect Lipid Membranes from Disruption by Aβ42", ACS Chemical Neuroscience, 2015, vol. 6, pp. 1860-1869.

Ohmi K., et al., "Sanfilippo Syndrome Type B, a Lysosomal Storage Disease, is Also a Tauopathy," National Academy of Sciences, 2009, vol. 106(20), pp. 8332-8337.

Rocker, A.E., et al., "The Molecular Tweezer CLR01 Inhibits Ebola and Zika Virus Infection", Antiviral Research, 2018, vol. 152, pp. 26-35.

Sinha, S., et al., "Comparison of Three Amyloid assembly Inhibitors—the Sugar Scyllo-Inositol, the Polyphenol Epigallocatechin Gallate, and the Molecular tweezer CLR01", ACS Chemical Neuroscience, 2012, vol. 3, pp. 451-458.

Talbiersky, P., et al., "Molecular Clip and Tweezer Introduce New Mechanisms of Enzyme Inhibition", Journal of the American Chemical Society, 2008, vol. 130, No. 30, pp. 9824-9828.

U.S. Non-Final Office Action dated Apr. 14, 2023 in U.S. Appl. No. 17/050,406.

Vopel, T., "Inhibition of Huntingtin Aggregation by the Molecular Tweezer CLR01", Journal of the American Chemical Society, 2017, vol. 139, pp. 5640-5643.

Warburton, S., et al., "Examining the Proteins of Functional Retinal Lipofuscin Using Proteomic Analysis as a Guide for Understanding Its Origin," Molecular Vision, 2005, vol. 11, pp. 1122-1134.

Xu, N. et al., "Inhibition of Mutant αB Crystallin-Induced Protein Aggregation by a Molecular Tweezer", Journal of the American Heart Association, Jan. 1, 2017, vol. 6, e006182, pp. 1-13.

Zheng, X., et al., "Amyloid β-protein Assembly: The Effect of Molecular Tweezers CLR01 and CLR03", The Journal of Physical Chemistry B, 2015, vol. 119, pp. 4831-4841.

Office Action for JP Application No. 2020-560382 dated Sep. 19, 2023 with English translation.

Restriction Requirement for U.S. Appl. No. 17/255,963 dated Sep. 20, 2023.

\* cited by examiner

A

B

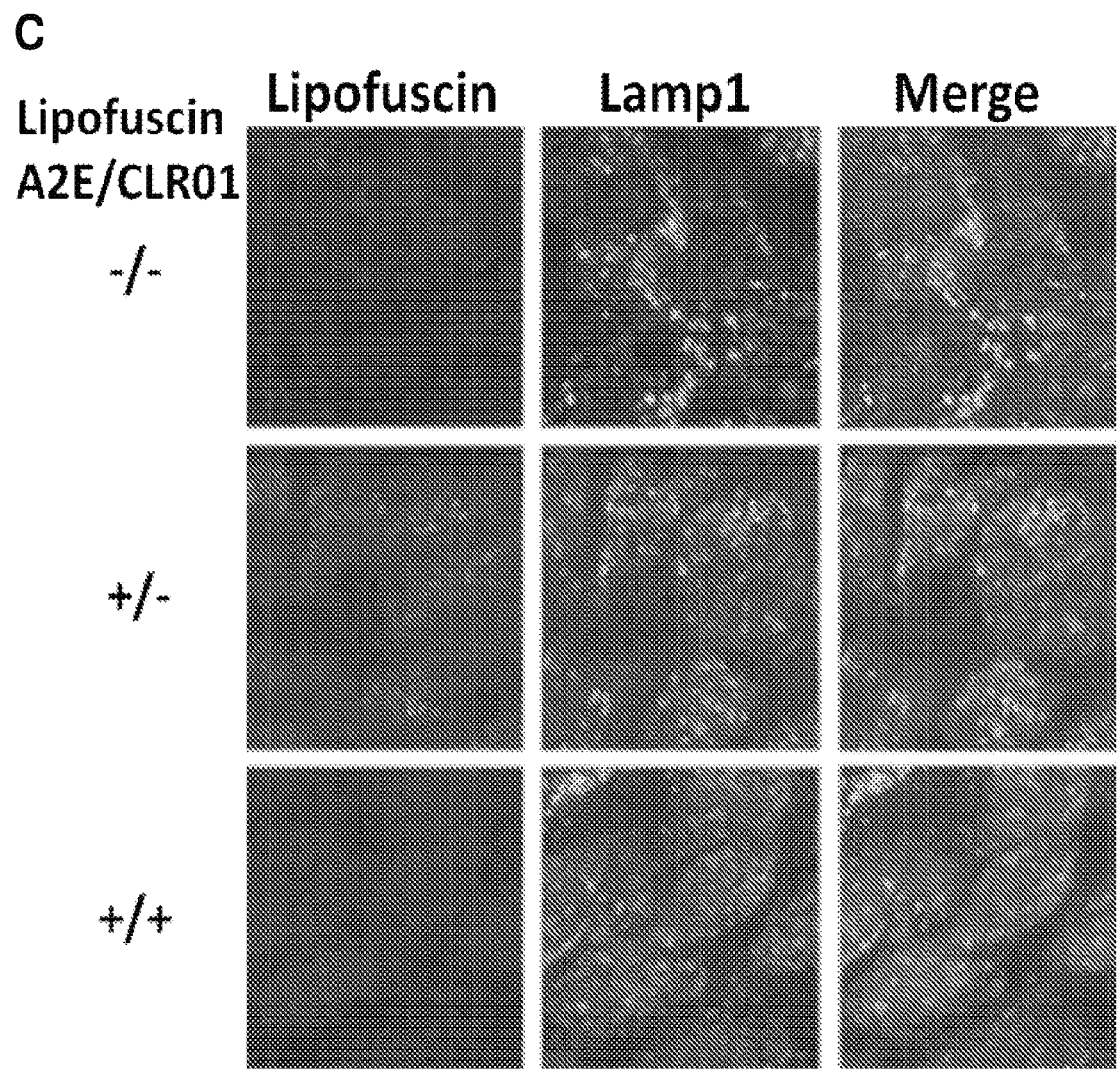
Fig. 1, cont'd.

INHIBITION OF LIPOFUSCIN AGGREGATION BY MOLECULAR TWEEZERS

CROSS-REFERENCE TO RELATED APPLICATIONS

This application claims priority to and benefit of U.S. Ser. No. 62/663,948, filed on Apr. 27, 2018, which is incorporated herein by reference in its entirety for all purposes.

STATEMENT OF GOVERNMENTAL SUPPORT

This application is a U.S. 371 National Phase of PCT/US2019/029221, filed on Apr. 25, 2019 which claims priority to and benefit of U.S. Ser. No. 62/663,948, filed on Apr. 27, 2018, both of which are incorporated herein by reference in their entirety for all purposes.

BACKGROUND

Lipofuscin is described as yellow-brown, autofluorescent pigment granules composed of residues of lysosomal digestion, including covalently cross-linked polypeptide chains and lipids. It is considered to be a "wear-and-tear" pigment and a sign of aging found in liver, kidney, heart muscle, retina, adrenals, nerve cells, and ganglion cells. Lipofuscin accumulation is a major risk factor implicated in macular degeneration and Stargardt disease, an inherited juvenile form of macular degeneration. Abnormal accumulation of lipofuscin also known as lipofuscinosis is associated with a family of neurodegenerative disorders—neuronal ceroid lipofuscinoses—the most common of which is Batten disease. In addition, pathological accumulation of lipofuscin is associated with certain lysosomal storage diseases, acromegaly, denervation atrophy, lipid myopathy, chronic obstructive pulmonary disease, and centronuclear myopathy. Accumulation of lipofuscin in the colon is the cause of melanosis coli (see, e.g., Hohn & Grune (2013) *Redox Biol.* 1: 140-144; Terman & Brunk (2004) *Free Radic. Res.* 40: 1335-1338; Uchida (2006) *Free Radic. Res.* 40: 1335-1338).

The accumulation of lipofuscin material affects primarily postmitotic cells and is involved in several physiopathological conditions (see, e.g., Jung et al. (2007) *Ann. N.Y. Acad. Sci.* 1119: 97-111; Brunk & Terman (2002) *Free Radic. Biol. Med.* 33(5): 611-6198). It is a recognized as a hallmark of aging. Abnormal storage of lipofuscin inside the lysosomal compartment is involved in a family of inherited neurodegenerative lysosomal storage disorders known as neuronal ceroid lipofuscinoses (Batten disease is the most common and severe forms of lipofuscinosis) (Fraldi et al. (2016) *Annu. Rev. Neurosci.* 39: 277-295; Mole et al. (2013) *Biochimica et Biophysica Acta (BBA)—Molecular Basis of Disease*, 1832(11): 1793-191210).

Lipofuscin toxicity also affects postmitotic cells such as cardiac myocytes or skeletal muscle cells and is therefore implicated in some myopathies such as lipid myopathy and centronuclear myopathy.

Pathogenesis of a number of other conditions such as chronic obstructive pulmonary disease, acromegaly and melanosis coli have been associated to abnormal accumulation of lipofuscin in affected tissues.

Importantly, lipofuscin accumulation within retinal pigment epithelial (RPE) cells (one of the tissues with the largest buildups of lipofuscin) is involved in the pathogenesis of a number of retinal diseases such as age-related macular degeneration and Stargardt disease, the most frequent form of inherited juvenile macular degeneration (Marcelo et al. (2017) *Lipofuscin Accumulation into and Clearance from Retinal Pigment Epithelium Lysosomes: Physiopathology and Emerging Therapeutics, Lysosomes—Associated Diseases and Methods to Study Their Function*, Dr. Pooja Dhiman (Ed.), InTech, DOI: 10.5772/intechopen.69304). The most common fluorophore present in the lipofuscin granules accumulating in retinal degenerative diseases is known as N-retinylidene-N-retinylethanolamine (also called A2E).

Attempts to generate pharmacological inhibitors of lipofuscin cytotoxicity in the context of eye diseases have included direct inhibitors of key visual cycle enzymes, RBP4 antagonists, primary amine-containing aldehyde traps, and deuterated analogs of vitamin A (Petrukhin, (2013) *Drug Discov. Today Ther. Strateg.* 10: e11-e20). However, to our knowledge, direct inhibition of the aggregation of it components or pharmacological treatment resulting in decrease of lipofuscin aggregates, has not been attempted.

SUMMARY

Molecular tweezers are inhibitors of abnormal protein self-assembly into amyloid, as described in PCT Patent Application No: WO2010102248 and multiple publications (Attar & Bitan (2014) *Curr. Pharm. Des.* 20: 2469-2483; Schrader et al. (2016) *Chem. Commun. (Camb)*, 52: 11318-11334). Molecular tweezers have a horseshoe-shaped structure composed of two hydrocarbon arms capable of hydrophobic interactions with the alkyl side chains of Lysine residues, which get threaded through the central cavity. At their bridgehead, molecular tweezers have negatively charged groups, e.g. phosphates, which form ionic interactions with the positively charged ammonium or guanidinium groups of Lysine and Arginine, respectively. Molecular tweezers have been reported to exert their inhibitory activity over amyloid beta assembly and decrease Aβ-induced toxicity since they utilize the same types of interactions, hydrophobic and electrostatic, found in early amyloid beta assembly as well as Lysine-mediated interaction of amyloid beta with cell membranes. However, because the association of polypeptide chains to each other in amyloid is non-covalent, and because their known mechanism of action involves interference with weak, non-covalent binding, prior to the experiments described herein molecular tweezers could not be expected to inhibit the formation of lipofuscin, which is a highly oxidized cross-linked aggregate consisting of oxidized protein (30-58%) and lipid (19-51%) clusters.

Surprisingly, however, the present inventors demonstrated that the molecular tweezers CLR01 inhibits lipofuscin accumulation and aggregation in retinal cells, suggesting that it may be used to combat Stargardt disease, macular degeneration, and other lipofuscin-related disorders including, but not limited to numerous lipofuscinoses.

Accordingly, various embodiments contemplated herein may include, but need not be limited to, one or more of the following:

Various embodiments contemplated herein may include, but need not be limited to, one or more of the following:

Embodiment 1: A method of treating a lipofuscin-related disorder in a mammal, said method comprising:
  administering to said mammal an effective amount of a molecular tweezers that is capable of inhibiting protein aggregation.

Embodiment 2: The method of embodiment 1, wherein said molecular tweezers is capable of inhibiting lipofuscin aggregation.

Embodiment 3: The method according to any one of embodiments 1-2, wherein said effective amount is an amount effective to delay the onset of, or to slow the progression, or stop, or to reverse lipofuscin accumulation/aggregation associated with said lipofuscin-related disorder.

Embodiment 4: The method according to any one of embodiments 1-3, wherein said effective amount is an amount effective to ameliorate one or more symptoms of the lipofuscin-related disorder.

Embodiment 5: The method according to any one of embodiments 1-3, wherein said effective amount is an amount effective to delay or stop the onset of, or to slow, or to stop, or to reverse progression of the lipofuscin-related disorder.

Embodiment 6: The method according to any one of embodiments 1-5, where said lipofuscin-related disorder is selected from the group consisting of a lipofuscin-related disorder associated with an eye disease, a neuronal ceroid lipofuscinosis (e.g. Batten disease), acromegaly, amyotrophic lateral sclerosis, denervation atrophy, lipid myopathy, chronic obstructive pulmonary disease, centronuclear myopathy, and melanosis coli.

Embodiment 7: The method according to any one of embodiments 1-6, wherein said lipofuscin-related disorder is a lipofuscin-related disorder associated with an eye disease.

Embodiment 8: The method of embodiment 7, wherein said eye disease comprises a disease selected from the group consisting of age-related macular degeneration, Stargardt disease, vitelliform macular degeneration (Best's macular dystrophy), retinal pigment epitheliopathy associated with choroidal melanoma, and severe ocular trauma.

Embodiment 9: The method of embodiment 6, wherein said eye disease is characterized by macular degeneration.

Embodiment 10: The method of embodiment 9, wherein said amelioration of one or more symptoms comprises an amelioration of one or more symptoms selected from the group consisting of drusen or waste deposits on the surface of the retina, changes in color (pigment) of the macula, blurred or fuzzy vision, the illusion that straight lines are wavy; the illusion that some objects are smaller than they really are, the appearance of a gray, dark or empty area in the center of the visual field, and fading of color vision.

Embodiment 11: The method of embodiment 9, wherein said administration is effective to delay the onset of, or to slow, stop, or reverse one or more processes selected from the group consisting of formation of drusen or waste deposits on the surface of the retina, changes in color (pigment) of the macula, blurring of fuzziness of vision; the illusion that straight lines are wavy; the illusion that some objects are smaller than they really are, the appearance of a gray, dark or empty area in the center of the visual field, and fading of color vision.

Embodiment 12: The method of embodiment 6, wherein said eye disease comprises Stargardt disease.

Embodiment 13: The method of embodiment 12, wherein said amelioration of one or more symptoms comprises an amelioration of one or more symptoms selected from the group consisting of blurry or distorted vision, inability to see in low lighting, difficulty recognizing familiar faces, and loss of color vision.

Embodiment 14: The method of embodiment 12, wherein said administration is effective to slow, stop, or reverse one or more processes selected from the group consisting of blurry or distortion of vision, inability to see in low lighting, difficulty recognizing familiar faces, and loss of color vision.

Embodiment 15: The method according to any one of embodiments 1-5, wherein said lipofuscin-related disorder is a neuronal ceroid lipofuscinosis.

Embodiment 16: The method of embodiment 15, wherein said lipofuscin-related disorder comprises a lipofuscinosis selected from the group consisting of infantile NCL (Santavuori-Haltia disease), late Infantile NCL (Jansky-Bielschowsky disease, Juvenile NCL (CLN1, Batten disease), Adult NCL (Kufs disease), Finnish Late Infantile NCL, Variant Late Infantile NCL, CLN7 NCL, CLN8 NCL (Northern Epilepsy, progressive epilepsy with mental retardation (EPMR)), Turkish Late Infantile Variant NCL, Batten disease, and CLN10 NCL (Congenital, Cathepsin D Deficiency).

Embodiment 17: The method of embodiment 16, wherein said lipofuscinosis comprises Batten Disease.

Embodiment 18: The method according to any one of embodiments 15-17, wherein said amelioration of one or more symptoms comprises an amelioration of one or more symptoms selected from the group consisting of cognitive dysfunction, movement/locomotor dysfunction, and vision loss.

Embodiment 19: The method according to any one of embodiments 15-17, wherein said administration is effective to slow, stop, or reverse one or more processes selected from the group consisting of progression of cognitive dysfunction, progression of movement/locomotor dysfunction, and progression of vision loss.

Embodiment 20: The method according to any one of embodiments 1-5, wherein said lipofuscin-related disorder is selected from the group consisting of acromegaly, amyotrophic lateral sclerosis, denervation atrophy, lipid myopathy, chronic obstructive pulmonary disease, centronuclear myopathy, and melanosis coli.

Embodiment 21: The method according to any one of embodiments 1-20, wherein said molecular tweezers is a molecular tweezers according to any one of formulas I to IV:

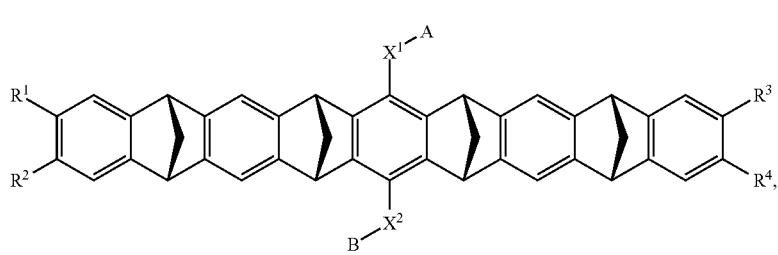

(I)

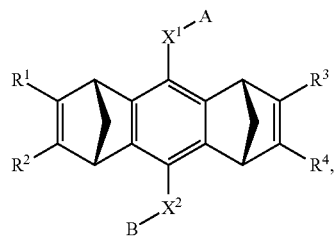

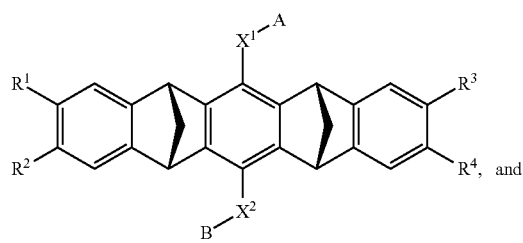

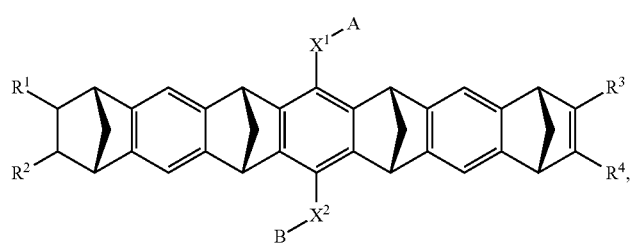

or a pharmaceutically acceptable salt, ester, amide, or prodrug thereof, wherein:

X$^1$ and X$^2$ are both O;

A alone, or A combined with X$^1$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate, and

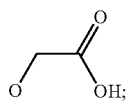

B alone, or B combined with X$^2$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate and

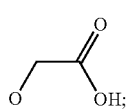

and each of R$^1$, R$^2$, R$^3$, and R$^4$ is, independently, selected from the group consisting of H, Cl, Br, I, OR, NR$_2$, NO$_2$, CO$_2$H, and CO$_2$R$^5$, wherein R$^5$ is alkyl, aryl or H, or R$^1$ and R$^2$ combine to form an aliphatic or aromatic ring, and/or R$^3$ and R$^4$ combine to form an aliphatic or aromatic ring.

Embodiment 22: The method of embodiment 21, wherein A and B are independently selected from the group consisting of

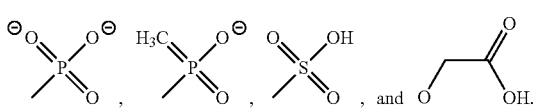

Embodiment 23: The method of embodiments 22, wherein A and B are the same.

Embodiment 24: The method of embodiment 21, wherein A and B are independently selected from the group consisting of

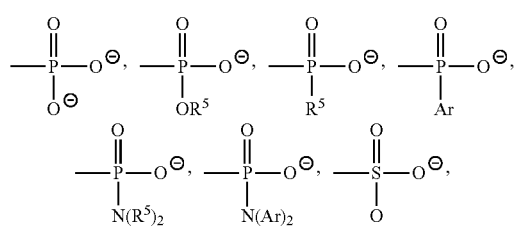

and —(CH$_2$)$_n$—CO$_2$$^-$, where R$^5$ is alkyl or H; n ranges from 1 to 10, and Ar is aryl.

Embodiment 25: The method of embodiments 24, wherein A and B are the same.

Embodiment 26: The method according to any one of embodiments 21-25, wherein said molecular tweezers is a molecular tweezers according formula I or a pharmaceutically acceptable salt thereof.

Embodiment 27: The method according to any one of embodiments 21-25, wherein said molecular tweezers is a molecular tweezers according formula II or a pharmaceutically acceptable salt thereof.

Embodiment 28: The method according to any one of embodiments 21-25, wherein said molecular tweezers is a molecular tweezers according formula III or a pharmaceutically acceptable salt thereof.

Embodiment 29: The method according to any one of embodiments 21-25, wherein said molecular tweezers is a molecular tweezers according formula IV or a pharmaceutically acceptable salt thereof.

Embodiment 30: The method of embodiment 21, wherein said molecular comprises a compound according to the formula:

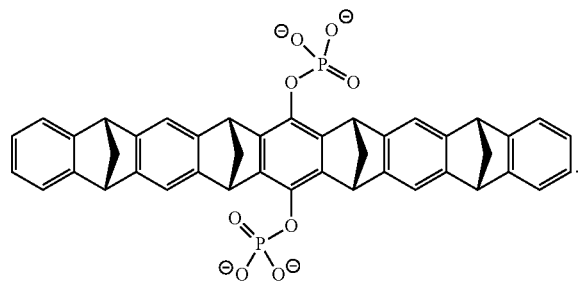

(TW1/CLR01)

Embodiment 31: The method of embodiment 21, wherein said molecular comprises a compound according to the formula:

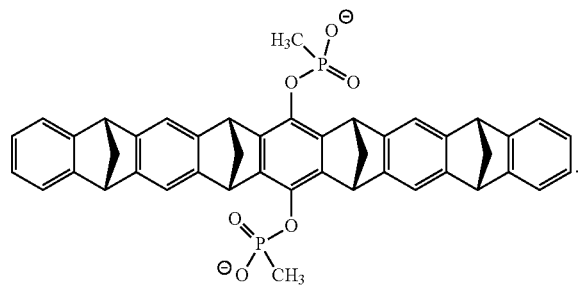

(TW2)

Embodiment 32: The method of embodiment 21, wherein said molecular comprises a compound according to the formula:

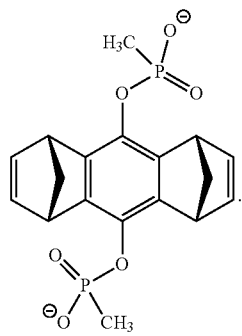

(TW3)

Embodiment 33: The method of embodiment 21, wherein said molecular comprises a compound according to the formula:

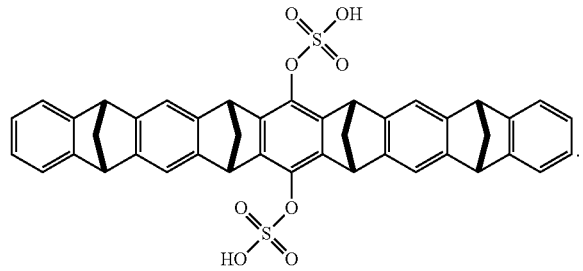

(TW4)

Embodiment 34: The method of embodiment 21, wherein said molecular comprises a compound according to the formula:

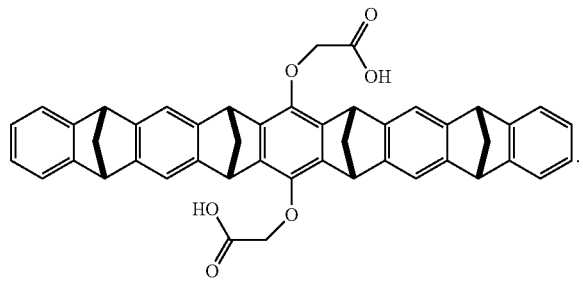

(TW5)

Embodiment 35: The method according to any one of embodiments 1-34, wherein said administration is via a route selected from the group consisting of oral delivery, isophoretic delivery, transdermal delivery, parenteral delivery, aerosol administration, administration via inhalation, intravenous administration, ocular administration, depot delivery (including subcutaneous/subdermal depot delivery), vaginal administration, and rectal administration.

Embodiment 36: The method according to any one of embodiments 1-34, wherein said administration comprises ocular administration.

Embodiment 37: The method of embodiment 36, wherein said ocular administration comprises administration via a route selected from the group consisting of topical ocular administration, topical ocular administration in combination with systemic and/or oral administration, IVT injection, periocular administration, subconjunctival injection, sub-tenon injection, intravitreal injection, subretinal administration and retrobulbar injection.

Embodiment 38: The method according to any one of embodiments 1-34, wherein said administration is parenteral.

Embodiment 39: The method of embodiment 38, wherein said administration comprise administration to the central nervous system.

Embodiment 40: The method of embodiment 39, wherein said administration is selected from a route selected from the group consisting of intraspinal administration, intrathecal or epidural administration, subdural administration, and administration is through a cannula.

Embodiment 41: The method of embodiment 38, wherein said administration is selected from a route selected from the group consisting of subcutaneous administration, intravenous administration, and administration through a subcutaneously implanted device.

Embodiment 42: The method according to any one of embodiments 1-41, wherein said mammal is a human.

Embodiment 43: The method according to any one of embodiments 1-41, wherein said mammal is non-human mammal.

Embodiment 44: A molecular tweezers for use in inhibiting lipofuscin aggregation, wherein said inhibiting lipofuscin aggregation comprises delaying the onset of, or slowing the progression of, or stopping, or reversing lipofuscin aggregation. (e.g., in a cell ex vivo, or in a mammal).

Embodiment 45: The molecular tweezers of embodiment 44, wherein said inhibiting lipofuscin aggregation comprises inhibiting protein aggregation in the treatment of a lipofuscin-related disorder in a mammal (e.g., said molecular tweezers is for use in the treatment of a lipofuscin-related disorder in a mammal).

Embodiment 46: The molecular tweezers according to any one of embodiments 44-45, wherein said molecular tweezers is capable of inhibiting lipofuscin aggregation.

Embodiment 47: The molecular tweezers according to any one of embodiments 44-46, wherein said treatment is effective to delay the onset of, or to slow the progression, or stop, or reverse lipofuscin accumulation/aggregation associated with said lipofuscin-related disorder.

Embodiment 48: The molecular tweezers according to any one of embodiments 44-47, wherein said treatment is effective to ameliorate one or more symptoms of said lipofuscin-related disorder.

Embodiment 49: The molecular tweezers according to any one of embodiments 44-47, wherein said treatment is effective to slow or delay the onset of, or to slow, or to stop, or to reverse progression of said lipofuscin-related disorder.

Embodiment 50: The molecular tweezers according to any one of embodiments 44-49, where said lipofuscin-related disorder is selected from the group consisting of a lipofuscin-related disorder associated with an eye disease, a neuronal ceroid lipofuscinosis (e.g. Batten disease), acromegaly, amyotrophic lateral sclerosis, denervation atrophy, lipid myopathy, chronic obstructive pulmonary disease, centronuclear myopathy, and melanosis coli.

Embodiment 51: The molecular tweezers according to any one of embodiments 44-50, wherein said lipofuscin-related disorder is a lipofuscin-related disorder associated with an eye disease.

Embodiment 52: The molecular tweezers of embodiment 51, wherein said eye disease comprises a disease selected from the group consisting of age-related macular degeneration, vitelliform macular degeneration (Best's macular dystrophy), retinal pigment epitheliopathy associated with choroidal melanoma, and severe ocular trauma.

Embodiment 53: The molecular tweezers of embodiment 52, wherein said lipofuscin-related disorder comprises macular degeneration.

Embodiment 54: The molecular tweezers of embodiment 53, wherein said amelioration of one or more symptoms comprises an amelioration of one or more symptoms selected from the group consisting of drusen or waste deposits on the surface of the retina, changes in color (pigment) of the macula, blurred or fuzzy vision, the illusion that straight lines are wavy; the illusion that some objects are smaller than they really are, the appearance of a gray, dark or empty area in the center of the visual field, and fading of color vision.

Embodiment 55: The molecular tweezers of embodiment 53, wherein said administration is effective to delay the onset of, or to slow, stop, or reverse one or more processes selected from the group consisting of formation of drusen or waste deposits on the surface of the retina, changes in color (pigment) of the macula, blurring of fuzziness of vision; the illusion that straight lines are wavy; the illusion that some objects are smaller than they really are, the appearance of a gray, dark or empty area in the center of the visual field, and fading of color vision.

Embodiment 56: The molecular tweezers of embodiment 52, wherein said eye disease comprises Stargardt disease.

Embodiment 57: The molecular tweezers of embodiment 56, wherein said amelioration of one or more symptoms comprises an amelioration of one or more symptoms selected from the group consisting of blurry or distorted vision, inability to see in low lighting, difficulty recognizing familiar faces, and loss of color vision.

Embodiment 58: The molecular tweezers of embodiment 56, wherein said administration is effective to slow, stop, or reverse one or more processes selected from the group consisting of blurry or distortion of vision, inability to see in low lighting, difficulty recognizing familiar faces, and loss of color vision.

Embodiment 59: The molecular tweezers according to any one of embodiments 44-50, wherein said lipofuscin-related disorder is a neuronal ceroid lipofuscinosis.

Embodiment 60: The molecular tweezers of embodiment 59, wherein said lipofuscin-related disorder comprises a lipofuscinosis selected from the group consisting of infantile NCL (Santavuori-Haltia disease), late Infantile NCL (Jansky-Bielschowsky disease, Juvenile NCL (CLN1, Batten disease), Adult NCL (Kufs disease), Finnish Late Infantile NCL, Variant Late Infantile NCL, CLN7 NCL, CLN8 NCL (Northern Epilepsy, progressive epilepsy with mental retardation (EPMR)), Turkish Late Infantile Variant NCL, Batten disease, and CLN10 NCL (Congenital, Cathepsin D Deficiency).

Embodiment 61: The molecular tweezers of embodiment 60, wherein said lipofuscinosis comprises Batten Disease.

Embodiment 62: The molecular tweezers according to any one of embodiments 59-61, wherein said amelioration of one or more symptoms comprises an amelioration of one or more symptoms selected from the group consisting of cognitive dysfunction, movement/locomotor dysfunction, and vision loss.

Embodiment 63: The molecular tweezers according to any one of embodiments 59-61, wherein said administration is effective to slow, stop, or reverse one or more processes selected from the group consisting of progression of cognitive dysfunction, progression of movement/locomotor dysfunction, and progression of vision loss.

Embodiment 64: The molecular tweezers according to any one of embodiments 44-50, wherein said lipofuscin-related disorder is selected from the group consisting of acromegaly, amyotrophic lateral sclerosis, denervation atrophy, lipid myopathy, chronic obstructive pulmonary disease, centronuclear myopathy, and melanosis coli.

Embodiment 65: The molecular tweezers according to any one of embodiments 44-64, wherein said molecular tweezers is a molecular tweezers according to any one of formulas I to IV:

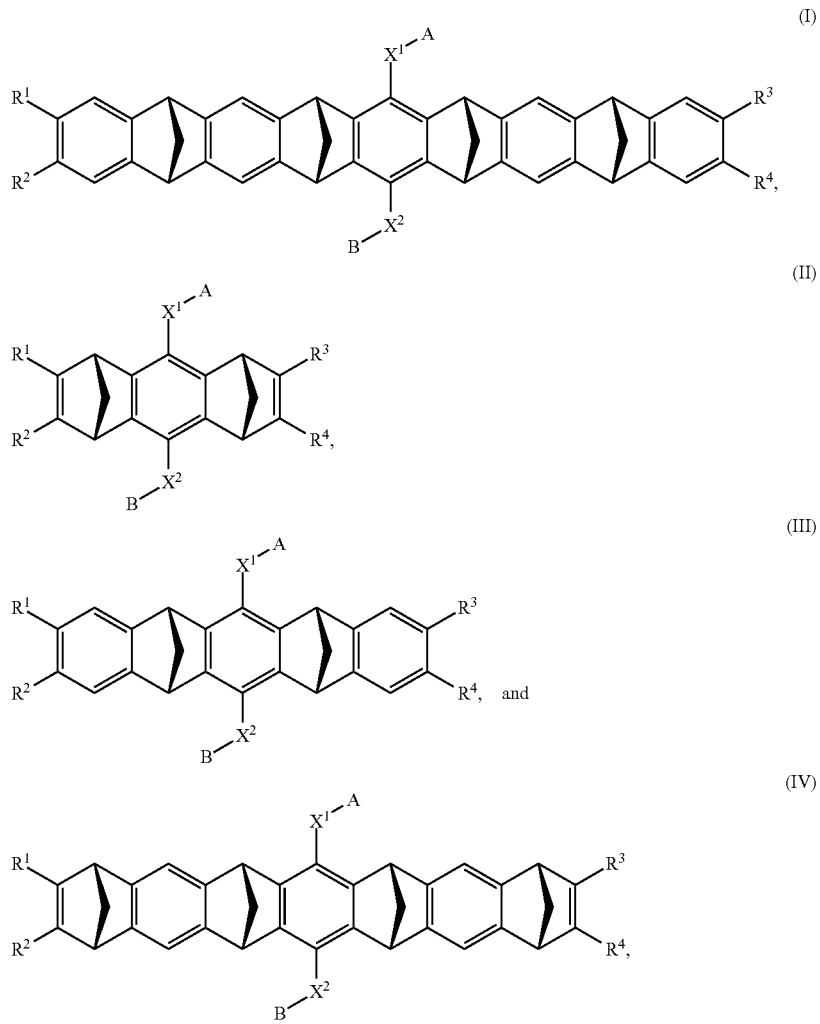

or a pharmaceutically acceptable salt, ester, amide, or prodrug thereof, wherein:

$X^1$ and $X^2$ are both O;

A alone, or A combined with $X^1$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate, and

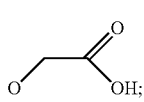

B alone, or B combined with $X^2$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate and

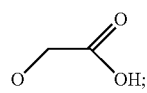

and each of $R^1$, $R^2$, $R^3$, and $R^4$ is, independently, selected from the group consisting of H, Cl, Br, I, OR, $NR_2$, $NO_2$, $CO_2H$, and $CO_2R^5$, wherein $R^5$ is alkyl, aryl or H, or $R^1$ and $R^2$ combine to form an aliphatic or aromatic ring, and/or $R^3$ and $R^4$ combine to form an aliphatic or aromatic ring.

Embodiment 66: The molecular tweezers of embodiment 65, wherein A and B are independently selected from the group consisting of

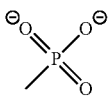 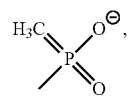  and

-continued

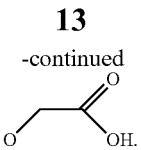

Embodiment 67: The molecular tweezers of embodiments 66, wherein A and B are the same.

Embodiment 68: The molecular tweezers of embodiment 65, wherein A and B are independently selected from the group consisting of

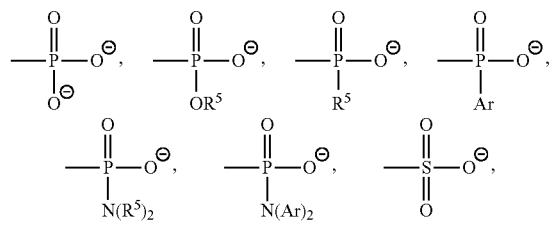

and —$(CH_2)_n$—$CO_2^-$, where $R^5$ is alkyl or H; n ranges from 1 to 10, and Ar is aryl.

Embodiment 69: The molecular tweezers of embodiments 68, wherein A and B are the same.

Embodiment 70: The molecular tweezers according to any one of embodiments 65-69, wherein said molecular tweezers is a molecular tweezers according formula I or a pharmaceutically acceptable salt thereof.

Embodiment 71: The molecular tweezers according to any one of embodiments 65-69, wherein said molecular tweezers is a molecular tweezers according formula II or a pharmaceutically acceptable salt thereof.

Embodiment 72: The molecular tweezers according to any one of embodiments 65-69, wherein said molecular tweezers is a molecular tweezers according formula III or a pharmaceutically acceptable salt thereof.

Embodiment 73: The molecular tweezers according to any one of embodiments 65-69, wherein said molecular tweezers is a molecular tweezers according formula IV or a pharmaceutically acceptable salt thereof.

Embodiment 74: The molecular tweezers of embodiment 65, wherein said molecular tweezers comprises a compound according to the formula:

(TW1/CLR01)

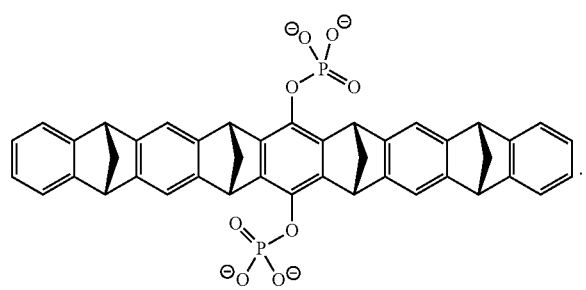

Embodiment 75: The molecular tweezers of embodiment 65, wherein said molecular tweezers comprises a compound according to the formula:

(TW2)

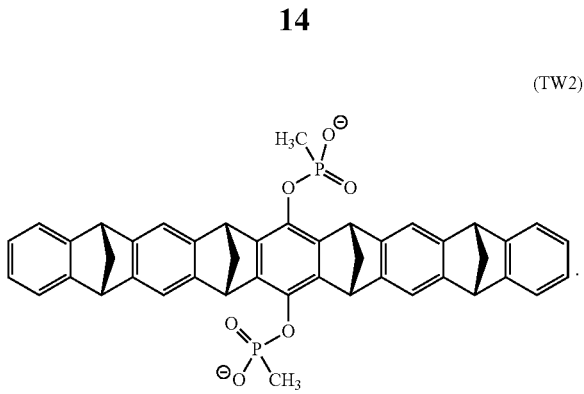

Embodiment 76: The molecular tweezers of embodiment 65, wherein said molecular tweezers comprises a compound according to the formula:

(TW3)

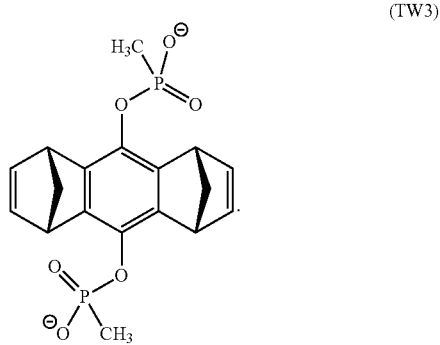 [SMILES: CP(=O)([O-])Oc1c2c(c(OP(C)(=O)[O-])c3c1[C@H]1C=C[C@@H]3C1)[C@H]1C=C[C@@H]2C1]

Embodiment 77: The molecular tweezers of embodiment 65, wherein said molecular tweezers comprises a compound according to the formula:

(TW4)

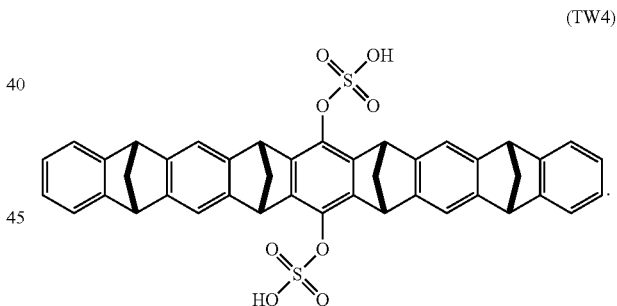

Embodiment 78: The molecular tweezers of embodiment 65, wherein said molecular tweezers comprises a compound according to the formula:

(TW5)

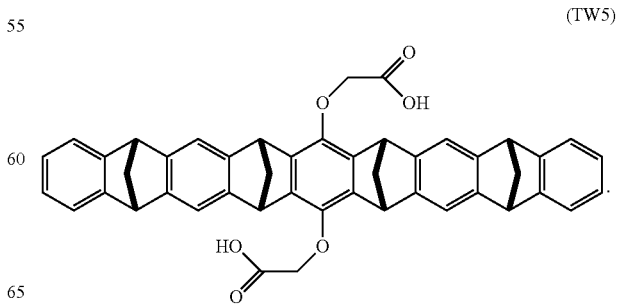

Embodiment 79: The molecular tweezers according to any one of embodiments 44-78, treatment comprises administration is via a route selected from the group consisting of oral delivery, isophoretic delivery, transdermal delivery, parenteral delivery, aerosol administration, administration via inhalation, intravenous administration, ocular administration, depot delivery (including subcutaneous/subdermal depot delivery), vaginal administration, and rectal administration.

Embodiment 80: The molecular tweezers according to any one of embodiments 44-78, wherein treatment comprises ocular administration.

Embodiment 81: The molecular tweezers of embodiment 80, wherein said ocular administration comprises administration via a route selected from the group consisting of topical ocular administration, topical ocular administration in combination with systemic and/or oral administration, IVT injection, periocular administration, subconjunctival injection, subtenon injection, intravitreal injection, subretinal administration and retrobulbar injection.

Embodiment 82: The molecular tweezers according to any one of embodiments 44-78, wherein said administration is parenteral.

Embodiment 83: The molecular tweezers of embodiment 82, wherein said administration comprise administration to the central nervous system.

Embodiment 84: The molecular tweezers of embodiment 83, wherein said administration is selected from a route selected from the group consisting of intraspinal administration, intrathecal or epidural administration, subdural administration, and administration is through a cannula.

Embodiment 85: The molecular tweezers of embodiment 82, wherein said administration is selected from a route selected from the group consisting of subcutaneous administration, intravenous administration, and administration through a subcutaneously implanted device.

Embodiment 86: The molecular tweezers according to any one of embodiments 44-85, wherein said mammal is a human.

Embodiment 87: The molecular tweezers according to any one of embodiments 44-85, wherein said mammal is non-human mammal.

Embodiment 88: The molecular tweezers according to any one of embodiments 44-87, wherein said molecular tweezers is provided as a pharmaceutical formulation comprising said molecular tweezers.

In certain embodiments the molecular tweezers used in the methods provided herein expressly exclude TW3. In certain embodiments, the subjects treated using the methods described herein are not diagnosed with and/or under treatment for a pathology characterized by aggregation of a protein selected from the group consisting of Aβ, tau, and α-synuclein. In certain embodiments, the subjects treated using the methods described herein are not diagnosed with and/or under treatment for a condition selected from the group consisting of Alzheimer's disease, amyloid mediated mild cognitive impairment (MCI), brain or spinal cord injury (including, but not limited to stroke), Huntingtin's Disease, and Parkinson's disease.

Definitions

Molecular tweezers, are host molecules with open cavities capable of binding guest molecules (see, e.g., Hardouin-Lerouge et al. (2011) Chem. Soc. Rev. 40: 30-43). The open cavity of the molecular tweezers may bind guests using non-covalent bonding which can include one or more of hydrogen bonding, metal coordination, hydrophobic forces, van der Waals forces, 7-7 interactions, and/or electrostatic effects. These complexes can be viewed as a subset of macrocyclic molecular receptors and their typical structure is characterized by two "arms" that bind the guest molecule between them and are only connected at one end leading to a certain flexibility of these molecules (induced fit model).

Lipofuscin is a highly oxidized cross-linked aggregate consisting of oxidized protein (30-58%) and lipid (19-51%) clusters (Jung et al. (2007) Ann. N.Y. Acad. Sci. 1119:97-111). It is a yellow-brown material accumulating overtime. Proteins within lipofuscin are linked by intramolecular and intermolecular cross-links. Many of these cross-links are caused by nonproteineous compounds including oxidation products of other cellular components, such as 4-hydoxy-2-nonenal (HNE). The so formed final product is resistant to degradation by cellular proteolytic systems. In general, such a material is referred to as lipofuscin, however other terms include ceroid, ceroid-like pigments, or age pigments.

The intracellular rate of lipofuscin formation is negatively correlated with the life expectancy of a postmitotic cell and increases with age. The higher the rate of intracellular lipofuscin accumulation over time, the shorter the future lifetime of the cell. Because there is no specific lipofuscin antibody and the composition varies between different cell types, using lipofuscin autofluorescence has become one of the most important methods of detection and quantification (Terman & Brunk (2004) Int. J. Biochem. Cell Biol. 36: 1400-1404). Other methods include some classical histochemical lipid-staining techniques and agents, such as Sudan black, Nile and Berlin blue, ferric ferrycianide, FontanaMasson, Ziehl-Neelsen, hematoxilin, eosin, or osmic acid. The typical fluorescence emission spectrum of lipofuscin extends from 570-605 nm when excited at 366 nm. Such a spectrum is probably caused by reactions between carbonyls and amino groups that result in Schiff bases, such as 1,4-dihydropyridines or 2-hydroxy-1,2-dihydropyrrol-3-ones, showing an autofluorescence that is similar to that of lipofuscin. In retinal pigment epithelial cells, a lipofuscin fluorophore (A2-E) is formed as the result of the reaction of retinal derivatives, showing a Schiff base structure (N-retinyl-N-retinylidene ethanolamine).

The term "lipofuscin-related disorder" refers to a pathology in which lipofuscin aggregated and/or where the amount of intra-cellular lipofuscin aggregations is greater than in a normal healthy mammal of the same gender, age, and species. Lipofuscin-related disorders particularly refers to disorders in which the lysosomal and proteosomal capacity to clear the cytosol from oxidized protein(s) is decreased as a consequence of the ageing process (e.g., in postmitotic aging cells), during oxidative stress, in the progression of pathologic events, or in lipofuscinoses, which are lysosomal storage diseases including, but not limited to, Batten's disease. As a consequence some oxidatively damaged intra-cellular proteins are not immediately degraded but further oxidized, resulting in the intracellular accumulation of lipofuscin which is characterized by a chemically reactive surface that can disturb cellular metabolism with toxic consequences to the cell as well as drive further protein and lipid peroxidation and formation of more lipofuscin. Permanently dividing, short-living cells, such as bone marrow or mucosa epithelia cells, have the ability to dilute the accumulated lipofuscin by cell division. In contrast, postmitotic cells, such as neurons, cardiac myocytes, or skeletal muscle cells, are not able to do so. In the eye, the RPE is one of the tissues with the largest buildups of lipofuscin. RPE lipofuscin increases with age in all healthy eyes. The lipofuscin localizes in lysosomal bodies of the RPE and can occupy ~20% of the cytoplasmic space by 80 years of age. The A2-E-fluorophore found in lipofuscin accumulates in retinal cells not only in age-dependent macular degeneration but in many other pathological processes. Buildup of lipofuscin in RPE lysosomes often evolves into irreversible damage of overlying photoreceptors. This is a common event in individuals with mutations in the ABCA4 gene, e.g., individuals with Stargardt's disease and is believed to underlie the progression of age-related lesions in people with AMD, the most common cause of blindness in the elderly population.

Illustrative lipofuscin-related disorders include but are not limited to lipofuscin-related disorders associated with an eye disease (e.g., age-related macular degeneration, vitelliform macular degeneration (Best's macular dystrophy), retinal pigment epitheliopathy associated with choroidal melanoma, severe ocular trauma; and the like), a neuronal ceroid lipofuscinosis (e.g. Batten disease), acromegaly, denervation atrophy, lipid myopathy, chronic obstructive pulmonary disease, centronuclear myopathy, melanosis coli, and the like. In certain embodiments "lipofuscin-related-disorders" expressly exclude Alzheimer's disease, and/or Parkinson's Disease. In certain embodiments lipofuscin-related disorders comprises pathologies in which lipofuscin has a pathogenic role.

The terms "subject," "individual," and "patient" may be used interchangeably and refer to humans, the as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from a lysosomal storage disorder or is at a risk of suffering a lysosomal storage disorder (e.g., as indicated by a genetic and/or metabolic marker).

The terms "treatment," "treating," or "treat" as used herein, refer to actions that produce a desirable effect on the symptoms or pathology of a lysosomal storage disease as described herein, and may include, but are not limited to, even minimal changes or improvements in one or more symptoms and/or one or more measurable markers of the disease or condition being treated. "Treatment," "treating," or "treat" does not necessarily indicate complete eradication or cure of the disease or condition, or associated symptoms thereof. In one embodiment, treatment comprises improvement of at least one symptom of a disease being treated. The improvement may be partial or complete. The subject receiving this treatment is any subject in need thereof. Exemplary markers of clinical improvement will be apparent to persons skilled in the art.

An "effective amount" refers to an amount effective, at dosages and for periods of time necessary, to achieve the desired therapeutic or prophylactic result. A "therapeutically effective amount" of molecular tweezers or formulation thereof described herein may vary according to factors such as the disease state, age, sex, and weight of the individual, and the ability of the treatment to elicit a desired response in the individual. A therapeutically effective amount is also one in which any toxic or detrimental effects of a treatment are substantially absent or are outweighed by the therapeutically beneficial effects. The term "therapeutically effective amount" refers to an amount of one or more molecular tweezers described herein or composition comprising the same that is effective to "treat" a lysosomal storage disorder in a mammal (e.g., a patient). In one embodiment, a therapeutically effective amount is an amount sufficient to improve at least one symptom associated with a lysosomal storage disorder.

A "prophylactically effective amount" refers to an amount effective, at dosages and for periods of time necessary, to achieve the desired prophylactic result, e.g., to slow or stop the onset of the disease or to slow or stop the onset of one or more symptoms of the disease. Typically, a prophylactic dose is administered prior to presentation of symptoms of the disease.

The term "mitigating" or "ameliorating" when used with respect to symptoms, refers to reduction or elimination of one or more symptoms of that pathology.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

The phrase "cause to be administered" refers to the actions taken by a medical professional (e.g., a physician), or a person prescribing and/or controlling medical care of a subject, that control and/or determine, and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The term "inhibiting protein aggregation" can refer to stopping or slowing the rate of protein aggregation and/or to inducing or accelerating disaggregation of an aggregated protein. Where protein aggregation contributes to accumulation of the aggregated protein the terms protein aggregation and protein accumulation can be used interchangeably. Method of detecting protein aggregation and/or accumulation are known to those of skill in the art and depend, in part, on the particular protein(s) aggregating.

BRIEF DESCRIPTION OF THE DRAWINGS

FIG. 2, panel B) Quantification of the data shown in panel B (N=15 per condition). Condition 1—negative control—20 µl of DMSO was added to the cells at t=0. After 10 h, the media was removed, the cells were washed with F12 medium, and new media was added. Condition 2—positive control—Lipofuscin A2E in DMSO at final concentration of 100 µM was added to the cells at t=0. After 10 h, the media was removed, the cells were washed with F12 medium, and new media was added. Condition 3—Lipofuscin A2E in DMSO was added to the cells at t=0. After 10 h, the media was removed, the cells were washed with F12 medium, and new media was added. CLR01 in PBS at final concentration of 100 µM was added at t=10 h.

DETAILED DESCRIPTION

Figure 1:
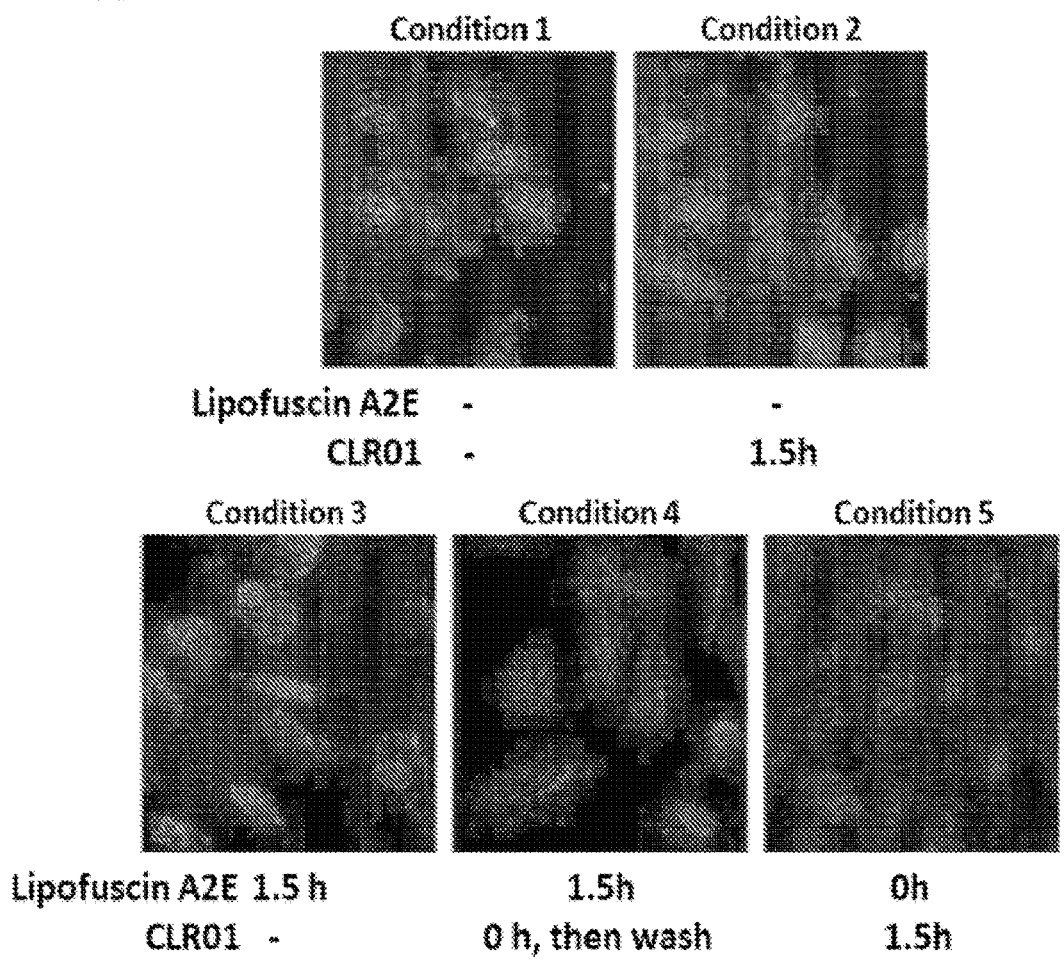
FIG. 1, panels A-C, shows that CLR01 inhibits lipofuscin accumulation and aggregation in ARPE-19 cells. Panel A) CLR01 in PBS and lipofuscin A2E were added to the cells at the indicated times. Cells were incubated up to 6 h in all cases and were imaged using a fluorescence microscope for visualization of lipofuscin autofluorecence (red) and cell nuclei (DAPI, blue). Panel B) Quantification of the data shown in panel A (N=15 per condition). C) Confocal microscopy images showing that lipofuscin colocalizes with the Lysosomal-membrane marker lamp1.
Figure 1:
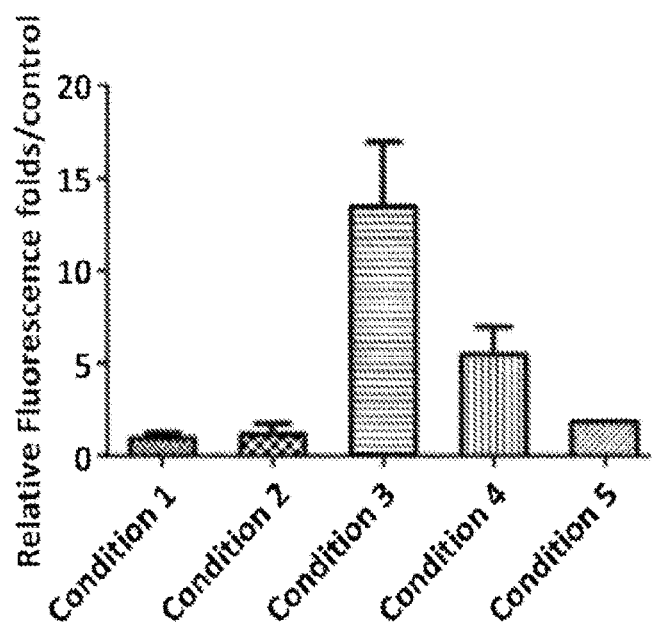

In various embodiments methods are provided for the use of molecular tweezers in the treatment and/or prophylaxis of lipofuscin-related disorders. In certain embodiments, the molecular tweezers are molecular tweezers that inhibit protein aggregation.

Molecular tweezers that inhibit abnormal protein self-assembly into amyloid, are described in PCT Publication No: WO 2010/102248 and in multiple publications (see, e.g., Attar & Bitan (2014) *Curr. Pharm. Des.* 20: 2469-2483; Schrader et al. (2016) *Chem. Commun.* (*Camb*), 52: 11318-113345, 6). However, because the association of polypeptide chains to each other in amyloid is non-covalent, and because their known mechanism of action involves interference with weak, non-covalent binding, prior to the work described herein, molecular tweezers could not be expected to inhibit the formation of lipofuscin aggregates.

As described herein in the Examples, cell culture experiments demonstrated that the molecular tweezer, CLR01 inhibits lipofuscin accumulation and aggregation in retinal cells, indicating that it may be used to combat Stargardt disease, macular degeneration, and other lipofuscin-related disorders. The data showed that the molecular tweezers CLR01 did not harm the cells and that when CLR01 was added to the cells and washed prior to addition of lipofuscin A2E, the fraction of CLR01 that presumably was internalized by the cells was sufficient to reduce the accumulation of lipofuscin aggregates at 6 h by ~60%. Moreover, when the cells were incubated first with lipofuscin A2E for 1 h and then exposed to CLR01, the accumulation of lipofuscin aggregates was reduced almost to the negative-control level demonstrating that the molecular tweezers CLR01 powerfully inhibits the formation of lipofuscin aggregates, presumably by allowing lysosomal degradation of the lipofuscin.

In view of these and other results, it is believed that molecular tweezers can be used for the treatment and/or prophylaxis of lipofuscin-related disorders. Accordingly, in various embodiments, methods for the treatment or prophylaxis of lipofuscin-related disorders are provided. In certain embodiments, the methods involve administering a therapeutically effective amount and/or a prophylactically effective amount of one or more molecular tweezers to a subject (e.g., a human or a non-human mammal) in need thereof. In certain embodiments, the subject "in need thereof" comprises a subject diagnosed with a lipofuscin-related disorder (e.g., a symptomatic subject) or a subject determined to be "at risk" for a lipofuscin-related disorders (e.g., an asymptomatic subject identified with one or more genetic markers or biochemical markers of a lipofuscin-related disorders). Typically, the molecular tweezers will be a molecular tweezers that inhibits protein aggregation. In certain embodiments the molecular tweezers can be a molecular tweezers that inhibits aggregation of lipofuscin.

In certain embodiments administration of the molecular tweezers is effective to slow the progression, or stop, or reverse accumulation/aggregation associated with the lipofuscin-related disorder. In certain embodiments the administration of the molecular tweezers is therapeutic and is effective to ameliorate one or more symptoms of the lipofuscin-related disorder. In certain embodiments the administration of the molecular tweezers is therapeutic and is effective to slow, or to stop, or to reverse progression of a lipofuscin-related disorder. In certain embodiments administration of the molecular tweezers is prophylactic and is effective to delay or stop the onset of the lipofuscin-related disorder or to delay or stop the onset of one or more symptoms of lipofuscin-related disorders.

Molecular Tweezers for the Treatment and/or Prophylaxis of Lipofuscin-Related Pathologies.

In various embodiments molecular tweezer(s) useful in the methods described herein may be capable of inhibiting and/or modulating aggregation of one or more proteins, and/or promoting disaggregation of protein fibrils or other protein aggregates, or both. In certain embodiments, the molecular tweezers are capable of inhibiting and/or modulating aggregation of lipofuscin, and/or promoting disaggregation of lipofuscin fibrils or other lipofuscin aggregates, or both.

In certain illustrative, but non-limiting embodiments, treatment of subjects with lipofuscin-related pathologies with molecular tweezers may improve survival of neurons, and/or regeneration of neurons, and/or other outcomes in cells that are likely to die as a result of the lipofuscin-related disorder. Distinct cell types or groups of cells may respond to treatment with molecular tweezers with varying efficacy or varying responses. Treatment outcomes may also be observed at the systemic or organism level, including some aspects of functional recovery.

Examples of molecular tweezers are known in the art, e.g., in International Publication Number WO 2010/102248 (also published as US 2012/0108548), which is herein incorporated by reference in its entirety and, in particular for the molecular tweezers described therein (see, especially Table 2 therein).

Illustrative molecular tweezers useful in the methods described herein may be a molecular tweezers according to any one of Formulas I, II, III, and IV:

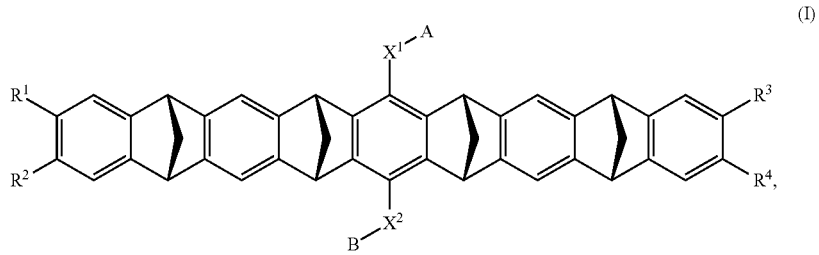

-continued (II)

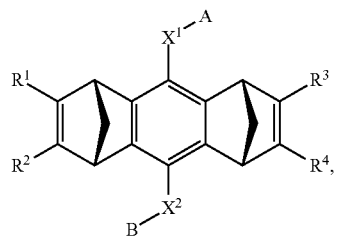

(III)

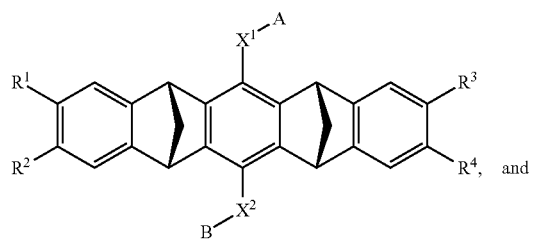

(IV)

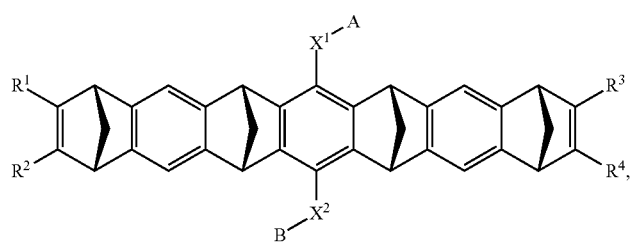

or a pharmaceutically acceptable salt, ester, amide, clathrate, or prodrug thereof, where: $X^1$ and $X^2$ are both O; A alone, or A combined with $X^1$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate, and

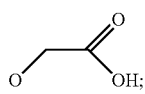

B alone, or B combined with $X^2$, forms a substituent selected from the group consisting of phosphate, hydrogen phosphate, alkylphosphonate, arylphosphonate, alkylphosphamide, arylphosphamide, sulfate, hydrogen sulfate, alkylcarboxylate and

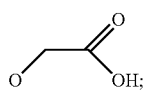

and each of $R^1$, $R^2$, $R^3$, and $R^4$ is, independently, selected from the group consisting of H, Cl, Br, I, OR, $NR_2$, $NO_2$, $CO_2H$, and $CO_2R^5$, wherein $R^5$ is alkyl, aryl or H, or R and $R^2$ combine to form an aliphatic or aromatic ring, and/or $R^3$ and $R^4$ combine to form an aliphatic or aromatic ring.

In certain embodiments A and B are independently selected from the group consisting of

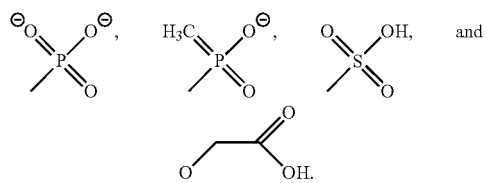

In certain embodiments A and B are the same. In certain embodiments A and B are independently selected from the group consisting of

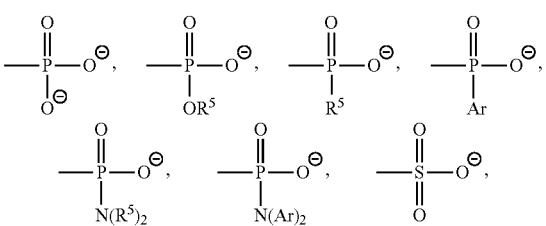

and $-(CH_2)_n-CO_2^-$, where R is alkyl or H; n ranges from 1 to 10, and Ar is aryl.

In certain embodiments the molecular tweezers is a molecular tweezers according formula I or a pharmaceutically acceptable salt thereof. In certain embodiments the molecular tweezers is a molecular tweezers according formula II or a pharmaceutically acceptable salt thereof. In certain embodiments the molecular tweezers is a molecular tweezers according formula III or a pharmaceutically acceptable salt thereof. In certain embodiments the molecular tweezers according formula IV or a pharmaceutically acceptable salt thereof. In certain embodiments the molecular tweezers comprises a compound according to the formula:

(TW1/CLR01)

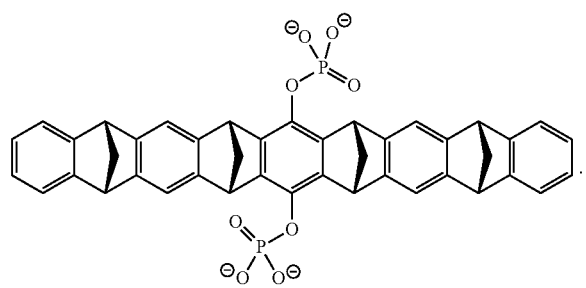

In certain embodiments the molecular tweezers comprises a compound according to the formula:

(TW2)

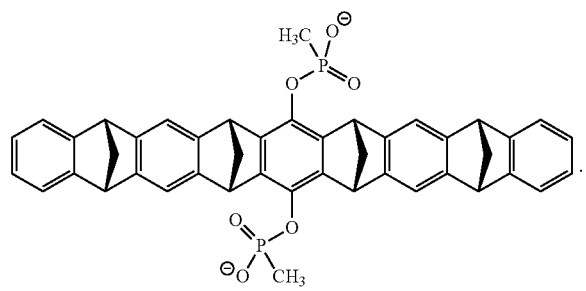

In certain embodiments the molecular tweezers comprises a compound according to the formula:

(TW3)

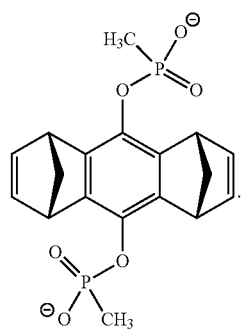

In certain embodiments the molecular tweezers comprises a compound according to the formula:

(TW4)

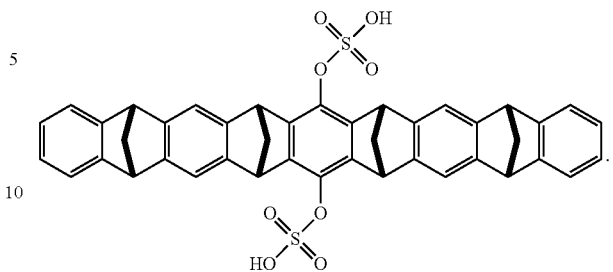

In certain embodiments the molecular tweezers comprises a compound according to the formula:

(TW5)

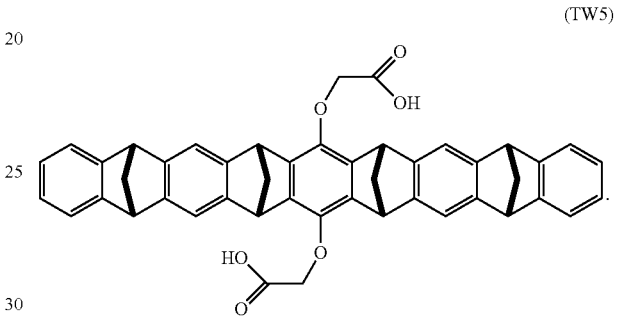

Other molecular tweezers are known in the art and using the teachings provided herein molecular tweezers well suited to use in the methods described herein will be readily available to one of skill in the art.

Synthesis of Molecular Tweezers

Molecular tweezers may be synthesized according to any of a number of methods known to those of skill in the art (see, e.g., Zimmerman et al. (1991) *J. Am. Chem. Soc.* 113: 183-196). The synthesis of molecular tweezers TW1 (i.e., CLR01), TW2, and TW3 is described below (see also PCT Application No: PCT/US2010/026419).

In one illustrative, but non-limiting embodiment, the skeleton of the tetramethylene-bridged molecular tweezers (the starting material of tweezers TW1 (i.e. CLR01) and TW2) can be constructed by repetitive Diels-Alder reactions of exo-5,6-bismethylene-2,3-benzonorbornene as diene with the bisnorbornadienobenzene as bisdieneophile. Subsequent oxidative dehydrogenation of the cyclohexene rings in the (1:2) Diels-Alder cycloadduct with DDQ leads to the molecular tweezers (Klärner et al. (1999) *Chem. Eur. J.* 5:1700-1707; Klärner et al. (2001) *Tetrahedron*, 57: 3573-3687; Klärner et al. (2004) *Eur. J. Org. Chem.* 7: 1405-1423; Klärner et al. (2008) *Synthesis of molecular tweezers and clips by the use of a molecular Lego set and their supramolecular functions*, Chapter 4:99-153, in *Strategies and Tactics in Organic Synthesis*, Vol. 7 (ed. Harmata, M.), Academic Press, Elsevier, Amsterdam).

The skeleton of the related dimethylene-bridged molecular clips can be synthesized by repetitive Diels-Alder reactions analogously to the synthesis of the tweezers using dibromo-o-quinodimethane derivatives as diene and the same bisdieneophile. In this case the HBr elimination in the (1:2) Diels-Alder cycloadduct occurs under the condition of formation leading to the molecular clips in a one-pot reaction.

In one illustrative embodiment, the bisdienophile is the starting material for the synthesis of the tweezers of type TW3. Their preparation starts with a one-pot reaction producing the norbornadienoquinone. The Diels-Alder cycloaddition of 1,3-cyclopentadiene to p-benzoquinone leads to the known (1:1) adduct which isomerizes in the presence of triethylamine to the corresponding hydroquinone that is subsequently oxidized with an excess of p-benzoquinone. The resulting quinone readily reacts with 1,3-cyclopentadiene at −78° C. almost quantitatively leading to a (60:40) mixture of the syn- and anti-Diels-Alder adduct which can be easily separated by recrystallization from toluene. Under basic conditions in the presence of acetic anhydride the syn-adduct is converted to the corresponding diacetoxy-substituted bisdienophile, the starting material of TW3.

The tweezers TW1-3 substituted by methanephosphonate or phosphate groups in the central benzene ring were prepared by reductive or basic ester hydrolysis of the corresponding diacetoxy derivatives followed by esterification of the hydroquinones with MePOCl 2 and $POCl_3$, respectively. Hydrolysis and neutralization of the methanephsphonic acid or phosphoric acid derivatives with lithium hydroxide lead to the desired methanephosphonate or phosphate salts (Fokkens et al. (2005) Chem. Eur. J. 11: 477-494; Schrader et al. (2005) J. Org. Chem. 70:10227-10237; Talbiersky et al. (2008) J. Am. Chem. Soc. 130:9824-9828).

Synthesis of TW-2 is described in Fokkens et al. (2005) J. Am. Chem. Soc. 27(41): 14415-14421, while the synthesis of various other molecular tweezers (including truncation variants) is described in Klärner et al. (2006) J. Am. Chem. Soc. 128(14): 4831-4841. The methods described therein can readily be modified to synthesize other molecular tweezers. These methods may be readily adapted or modified to prepare other molecular tweezers of the present invention.

Formulation and Administration of Molecular Tweezers

In some instances, delivery of a naked, i.e. native form, molecular tweezers may be sufficient to inhibit aggregation of a target protein in a cell (e.g., lipofuscin). In various embodiments, a molecular tweezers may be administered in the form of a salt, ester, amide, clathrate, derivative, and the like, provided the salt, ester, amide, clathrate, or derivative is pharmacologically effective (e.g., capable of inhibiting a protein aggregation (e.g., in certain embodiments, inhibiting aggregation of one or more of α-synuclein, A, and/or Tau). In certain embodiments a prodrug or other adduct or derivative of a molecular tweezers described herein is contemplated. Such prodrug(s), upon administration to a subject in need thereof, are capable of providing, directly or indirectly, the molecular tweezers.

In certain embodiments pharmaceutical compositions are provided, that comprise any one or more of the molecular tweezers described herein (or a prodrug, pharmaceutically acceptable salt, pharmaceutically acceptable ester, pharmaceutically acceptable amide, prodrug, or other pharmaceutically acceptable derivative thereof), and optionally comprise a pharmaceutically acceptable carrier. In certain embodiments, these compositions optionally further comprise one or more additional therapeutic agents. In certain embodiments a molecular tweezers described herein may be administered to a patient in need thereof in combination with the administration of one or more other therapeutic agents. For example, additional therapeutic agents for conjoint administration or inclusion in a pharmaceutical composition with a molecular tweezers described herein may be an approved agent to treat the same or related indication, or it may be any one of a number of agents undergoing approval in the Food and Drug Administration for a lipofuscin-related disorder.

Salts, esters, amides, clathrates, prodrugs and other derivatives of a molecular tweezers can be prepared using standard procedures known in the art of synthetic organic chemistry. For example, in certain embodiments, a pharmaceutically acceptable salt form of the molecular tweezers is contemplated. As used herein, the term "pharmaceutically acceptable salt" refers to those salts that are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, Berge, et al. (1977) J. Pharmaceutical Sciences, 66: 1-19, describe pharmaceutically acceptable salts in detail. The salts can be prepared in situ during the final isolation and purification of the active agents (e.g., molecular tweezers), or separately by reacting a free base or free acid function with a suitable reagent, as described generally below. For example, a free base function can be reacted with a suitable acid or a free acid function can be reacted with a suitable free base. Furthermore, where the compounds (such as the molecular tweezers) are or carry an acidic moiety, suitable pharmaceutically acceptable salts thereof may, include metal salts such as alkali metal salts, e.g. sodium, potassium, or copper salts; ammonium hydroxide, calcium hydroxide, trimethylamine, and the like; and alkaline earth metal salts, e.g. calcium or magnesium salts.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In certain embodiments, the compounds described herein can be formulated as "pharmaceutically acceptable esters". In certain embodiments suitable esters include, but are not limited to, esters that hydrolyze in vivo and include those that break down readily in the human body to leave the parent compound or a salt thereof. Suitable ester groups include, but are not limited to, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Preparation of esters may involve functionalization of, e.g., hydroxyl and/or carboxyl groups that are present within the molecular structure of a molecular tweezers. In certain embodiments, the esters are acyl-substituted derivatives of free alcohol groups, i.e., moieties derived from carboxylic acids of the formula RCOOH where R is alky, and preferably is lower alkyl. Esters may be reconverted to the free acids, if desired, by using conventional hydrogenolysis or hydrolysis procedures.

Amides may also be prepared using techniques known in the art. For example, an amide may be prepared from an ester using suitable amine reactants, or prepared from an anhydride or an acid chloride by reaction with ammonia or a lower alkyl amine.

In various embodiments any one or more of the molecular tweezers described herein may be combined with a pharmaceutically acceptable carrier (excipient) to form a pharmacological composition (pharmaceutical formulation). Certain pharmaceutically acceptable carriers can contain one or more physiologically acceptable compound(s) that act, e.g., to stabilize the composition, increase or decrease the absorption of the molecular tweezers, or improve penetration of the blood brain barrier (where appropriate). Physiologically acceptable compounds may include, e.g., carbohydrates (e.g., glucose, sucrose, or dextrans), antioxidants (e.g. ascorbic acid or glutathione), chelating agents, low molecular weight proteins, protection and uptake enhancers (e.g., lipids), compositions that reduce the clearance or hydrolysis of the active agents, or excipients or other stabilizers and/or buffers. Other physiologically acceptable compounds, particularly of use in the preparation of tablets, capsules, gel caps, and the like include, but are not limited to binders, diluents/fillers, disintegrants, lubricants, suspending agents, and the like. In certain embodiments, a pharmaceutical formulation may enhance delivery or efficacy of a molecular tweezers.

In various embodiments, a molecular tweezers described herein may be prepared for parenteral, topical, oral, nasal (or otherwise inhaled), rectal, or local administration. Administration may occur, for example, transdermally, or by aerosol.

A pharmaceutical composition comprising one or more molecular tweezers described herein may be administered in a variety of unit dosage forms depending upon the method of administration. Suitable unit dosage forms, include, but are not limited to, powders, tablets, pills, capsules, lozenges, suppositories, patches, nasal sprays, injectables, implantable sustained-release formulations, and lipid complexes.

In certain embodiments, an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), or an optional lubricant (e.g., talc, magnesium stearate, polyethylene glycol 6000, etc.), may be added to a molecular tweezers and the resulting composition may be compressed to manufacture an oral dosage form (e.g., a tablet). In particular embodiments, a compressed product may be coated, e.g., to mask the taste of the compressed product, to promote enteric dissolution of the compressed product, or to promote sustained release of the molecular tweezers. Suitable coating materials include, but are not limited to, ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds that may be included a pharmaceutical composition comprising one or more molecular tweezers may include wetting agents, emulsifying agents, dispersing agents or preservatives that are particularly useful for preventing the growth or action of microorganisms. Various preservatives are well known and include, for example, phenol and ascorbic acid. The choice of pharmaceutically acceptable carrier(s), including a physiologically acceptable compound, depends, e.g., on the route of administration of the molecular tweezers and on the particular physio-chemical characteristics of the molecular tweezers.

In certain embodiments, one or more excipients for use in a pharmaceutical composition including one or more molecular tweezers may be sterile and/or substantially free of undesirable matter. Such compositions may be sterilized by conventional techniques known in the art. For various oral dosage form excipients, such as tablets and capsules, sterility is not required. Standards are known in the art, e.g., the SUP/NF standard.

A pharmaceutical composition comprising one or more molecular tweezers as described herein may be administered in a single or in multiple administrations depending on the dosage, the required frequency of administration, and the known or anticipated tolerance of the subject for the pharmaceutical composition with respect to dosages and frequency of administration. In various embodiments, the composition may provide a sufficient quantity of a molecular tweezers to effectively treat (ameliorate one or more symptoms of) spinal cord injury or traumatic brain injury in the subject (e.g., decrease cellular impairment or cell death (e.g., neurodegeneration), improve functional recovery, and/or improve post-injury neuronal activities).

In some embodiments, the molecular tweezers is administered to a subject (e.g., a human or a non-human mammal) diagnosed with a lipofuscin-related disorder. In certain embodiments, such a subject is exhibiting one or more symptoms of a lipofuscin-related disorder. In certain embodiments the molecular tweezers is administered to a subject that is asymptomatic, but identified as being "at risk" for a lipofuscin-related disorder (e.g., a subject with one or more genetic or metabolic markers of a lipofuscin-related disorder). In certain embodiments, the molecular tweezers is administered to an infant. In certain embodiments, the molecular tweezers is administered to a subject before the appearance of symptoms of a lipofuscin-related disorder (e.g., in the case of humans within 3 months of birth, or within 6 months of birth, or within 1 year of birth, or within 2 years of birth, or within 3 years of birth, or within 4 years of birth, or within 5 years of birth, or within 6 years of birth, or before adolescence, etc., depending on the lipofuscin-related disorder being treated).

The amount and/or concentration of molecular tweezers to be administered to a subject may vary widely, and will typically be selected primarily based on activity of the molecular tweezers and the characteristics of the subject, e.g., species and body weight, as well as the particular mode of administration and the needs of the subject. In certain embodiments, the dosage of molecular tweezers may be 0.001 to about 50 or more mg/kg/day. For example, the dosage of a molecular tweezers may be about 0.001, 0.01, 0.1, 1, 5, 10, 20, 30, 40, or 50 or more mg/kg/day. In certain embodiments typical dosages range from about 1 mg/kg/day to about 3 mg/kg/day, from about 3 mg/kg/day to about 10 mg/kg/day, from about 10 mg/kg/day to about 20.0 mg/kg/day, or from about 20 mg/kg/day to about 50 mg/kg/day. In certain embodiments, dosages range from about 10 mg/kg/day to about 50 mg/kg/day. In certain embodiments, dosages range from about 20 mg to about 50 mg given orally twice daily. Dosages may be varied to optimize a therapeutic and/or prophylactic regimen in a particular subject or group of subjects.

In certain embodiments, a molecular tweezers is administered to the oral cavity, e.g., by the use of a lozenge, aerosol spray, mouthwash, coated swab, or other mechanism known in the art.

In certain embodiments a molecular tweezers may be administered systemically (e.g., orally, or as an injectable) in accordance with standard methods known in the art. In certain embodiments, the molecular tweezers may be delivered through the skin using a transdermal drug delivery systems, i.e., transdermal "patches," wherein the molecular tweezers are typically contained within a laminated structure that serves as a drug delivery device to be affixed to the skin. In such a structure, the drug composition is typically contained in a layer, or reservoir, underlying an upper backing layer. The reservoir of a transdermal patch includes a quantity of molecular tweezers that is ultimately available for delivery to the surface of the skin. Thus, the reservoir may include, e.g., the molecular tweezers of the present invention in an adhesive on a backing layer of the patch, or in any of a variety of different matrix formulations known in the art. The patch may contain a single reservoir or multiple reservoirs.

In one illustrative, but non-limiting, transdermal patch embodiment, a reservoir may comprise a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, and polyurethanes. Alternatively, the molecular tweezers-containing reservoir and skin contact adhesive are present as separate and distinct layers, with the adhesive underlying the reservoir which, in this case, may be either a polymeric matrix as described above, a liquid or hydrogel reservoir, or another form of reservoir known in the art. The backing layer in these laminates, which serves as the upper surface of the device, preferably functions as a primary structural element of the patch and provides the device with a substantial portion of flexibility. The material selected for the backing layer is preferably substantially impermeable to the molecular tweezers and to any other materials that are present.

Additional formulations for topical delivery include, but are not limited to, ointments, gels, sprays, fluids, and creams. Ointments are semisolid preparations that are typically based on petrolatum or other petroleum derivatives. Creams including a molecular tweezers are typically viscous liquids or semisolid emulsions, e.g. oil-in-water or water-in-oil emulsions. Cream bases are typically water-washable and include an oil phase, an emulsifier, and an aqueous phase. The oil phase, also sometimes called the "internal" phase, of a cream base is generally comprised of petrolatum and a fatty alcohol, e.g. cetyl alcohol or stearyl alcohol; the aqueous phase usually, although not necessarily, exceeds the oil phase in volume, and generally contains a humectant. The emulsifier in a cream formulation is generally a non-ionic, anionic, cationic, or amphoteric surfactant. The specific ointment or cream base to be used may be selected to provide for optimum drug delivery according to the art. As with other carriers or vehicles, an ointment base may be inert, stable, non-irritating, and non-sensitizing.

Various buccal and sublingual formulations are also contemplated.

In certain embodiments, administration of a molecular tweezers may be parenteral. Parenteral administration may include, for example, intraspinal, intrathecal, epidural, subdural, subcutaneous, or intravenous administration. Means of parenteral administration are known in the art. In particular embodiments, parenteral administration may include a subcutaneously implanted device.

In certain embodiments, it may be desirable to deliver the molecular tweezers to the brain and/or central nervous system (CNS). In certain embodiments involving system administration, this could require that the molecular tweezers cross the blood brain barrier. In various embodiments this may be facilitated by co-administering a molecular tweezers with carrier molecules such as cationic dendrimers or arginine-rich peptides, that may carry a molecular tweezers over the blood brain barrier.

In certain embodiments a molecular tweezers may be delivered directly to the brain by administration through the implantation of a biocompatible release system (e.g., a reservoir), by direct administration through an implanted cannula, by administration through an implanted or partially implanted drug pump, or mechanisms of similar function known the art. In certain embodiments, a molecular tweezers may be systemically administered (e.g., injected into a vein). In certain embodiments it is expected that the molecular tweezers will be transported across the blood brain barrier without the use of additional compounds included in a pharmaceutical composition to enhance transport across the blood brain barrier.

In certain embodiments, one or more molecular tweezers may be provided as a concentrate, e.g., in a storage container or soluble capsule ready for dilution or addition to a volume of water, alcohol, hydrogen peroxide, or other diluent. A concentrate may designed to provide a particular amount of molecular tweezers and/or a particular total volume. The concentrate may be formulated for dilution in a particular volume of diluents prior to administration.

In certain embodiments the molecular tweezers is formulated for ocular administration. The three primary methods of delivery of ocular medications to the eye are topical, local ocular (i.e., subconjunctival, intravitreal, retrobulbar, intracameral, subretinal), and systemic. The most appropriate method of administration depends on the area of the eye to be medicated. The conjunctiva, cornea, anterior chamber, and iris usually respond well to topical therapy. The eyelids can be treated with topical therapy but more frequently require systemic therapy. The posterior segment is typically achieved via systemic therapy, because most topical medications do not penetrate to the posterior segment. Retrobulbar and orbital tissues can be treated systemically. Subconjunctival or sub-Tenon's therapy, although not a true form of systemic medication administration, has the ability to increase both drug absorption and contact time. In certain embodiments the medications both leak onto the cornea from the entry hole of injection and diffuse through the sclera into the globe. Drugs with low solubility may provide a repository of drug lasting days to weeks. Appropriate amounts and formulation of medication should be used. Large amounts, especially of long-acting salts, can cause a significant inflammatory reaction. For sub-Tenon's injections, 0.5 mL per site is usually safe and effective in small animals, and <1 mL can be used in large animals such as horses and cows.

Retrobulbar medications can also be used for therapeutics. Whenever any medication is placed into the orbit, care must be taken to ensure that the medication is not inadvertently injected into a blood vessel, the optic nerve, or one of the orbital foramen.

Systemic medication can be used for posterior segment therapy and to complement topical therapy for the anterior segment. The blood-ocular barriers can limit absorption of less lipophilic drugs, but inflammation will initially allow greater drug concentrations to reach the site. As the eye starts to heal, these barriers will again become more effective and can limit further drug penetration.

In various embodiments after topical administration, up to 80% of the applied drug(s) is absorbed systemically across the highly vascularized nasopharyngeal mucosa. Because absorption via this route bypasses the liver, there is not the large first-pass metabolism seen after oral administration. Depending on the drugs used, this can result in systemic adverse effects.

Other suitable formulations and modes of administration are known or may be derived from the art.

In various embodiments, a molecular tweezers described herein may be administered to a mammal in need thereof, such as a mammal diagnosed as having or at risk for a lipofuscin-related disorder. In certain embodiments a molecular tweezers may be administered to inhibit aggregation of one or more proteins (e.g., lipofuscin). A molecular tweezers described herein may be administered to mitigate one or more symptoms of a lipofuscin-related disorder.

A therapeutically effective dose of a pharmaceutical composition of the present invention may depend upon the age of the subject, the gender of the subject, the species of the subject, the particular pathology, the severity of the symptoms, and the general state of the subject's health.

The pharmaceutical compositions described herein may be suitable for administration to an animal, e.g., for veterinary use. Accordingly, certain embodiments of the methods described herein may include administration of a pharmaceutical composition described herein non-human organisms, e.g., non-human mammals such as a non-human primates, canine, equine, feline, porcine, ungulate, lagomorphs, or other vertebrates. In various embodiments the pharmaceutical compositions are suitable for administration to a human.

Lipofuscin-Related Disorders for Treatment with Molecular Tweezers.

In various embodiments molecular tweezers are administered to a subject (e.g., to a mammal in need thereof) for the treatment or prophylaxis of a lipofuscin-related disorder. In certain embodiments the lipofuscin-related disorder comprises an ocular disease that is a lipofuscin-related disorder. In certain embodiments the lipofuscin-related disorder comprises a lipofuscinosis.

In certain embodiments the lipofuscin-related disorder comprises a disorder such as a lipofuscin-related disorder associated with an eye disease, a neuronal ceroid lipofuscinosis (e.g. Batten disease), acromegaly, amyotrophic lateral sclerosis, denervation atrophy, lipid myopathy, chronic obstructive pulmonary disease, centronuclear myopathy, melanosis coli, and the like. In certain embodiments the lipofuscin-related disorder is a lipofuscin-related disorder associated with an eye disease (e.g., age-related macular degeneration, vitelliform macular degeneration (Best's macular dystrophy), retinal pigment epitheliopathy associated with choroidal melanoma, severe ocular trauma, and the like).

Age-Related Macular Degeneration.

The accumulation of the autofluorescent pigment lipofuscin in the retina that occurs with aging has been explained as a side effect of the visual cycle. It occurs when two molecules of all-trans-retinal condense with one molecule of phosphatidylethanolamine in the discs of the rod outer segments, and is followed by uptake into retinal pigment epithelium (RPE) and conversion to the stable A2E, a pyridinium bisretinoid that is toxic to RPE cells. The accumulation of A2E, the major component of lipofuscin causes RPE cell apoptosis, thereby explaining age-related macular degeneration.

Age-related macular degeneration (AMD) is the most common cause of irreversible central vision loss in elderly patients. Dilated funduscopic findings are diagnostic; color photographs, fluorescein angiography, and optical coherence tomography assist in confirming the diagnosis and in directing treatment. AMD is the leading cause of permanent, irreversible vision loss in the elderly. Age related macular degeneration occurs in two forms: 1) Dry (nonexudative or atrophic); and 2) Wet (exudative or neovascular).

Dry AMD causes changes of the retinal pigment epithelium, typically visible as dark pinpoint areas. The retinal pigment epithelium plays a critical role in keeping the cones and rods healthy and functioning well. Accumulation of waste products from the rods and cones can result in drusen, which appear as yellow spots. Areas of chorioretinal atrophy (referred to as geographic atrophy) occur in more advanced cases of dry AMD. There is no elevated macular scar (disciform scar), edema, hemorrhage, or exudation.

In Dry AMD, the loss of central vision occurs over years and is painless, and most patients retain enough vision to read and drive. Central blind spots (scotomas) usually occur late in the disease and can sometimes become severe. Symptoms are usually bilateral. Funduscopic changes include, but are not limited to changes in the retinal pigment epithelium, Drusen, and areas of chorioretinal atrophy.

In wet AMD rapid vision loss occurs usually over days to week. The first symptom is usually visual distortion, such as a central blind spot (scotoma) or curving of straight lines (metamorphopsia). Peripheral vision and color vision are generally unaffected; however, the patient may become legally blind (<20/200 vision) in the affected eye, particularly if AMD is not treated.

In certain embodiments the prophylactic and/or therapeutic methods described herein involve ameliorating one or more of the above symptoms (e.g., one or more symptoms selected from the group consisting of drusen or waste deposits on the surface of the retina, changes in color (pigment) of the macula, blurred or fuzzy vision, the illusion that straight lines are wavy; the illusion that some objects are smaller than they really are, the appearance of a gray, dark or empty area in the center of the visual field, and fading of color vision), and/or delaying the onset, slowing, stopping, or reversing the progression of one or more of these symptoms.

Vitelliform Macular Degeneration

Vitelliform macular degeneration (a.k.a., vitelliform macular dystrophy) is a genetic eye disorder that can cause progressive vision loss. This disorder affects the retina. Specifically, vitelliform macular dystrophy disrupts cells in a small area near the center of the retina called the macula. Lipofuscin builds up in cells underlying the macula. Over time, the abnormal accumulation of this substance can damage cells that are critical for clear central vision. As a result, people with this disorder often lose their central vision, and their eyesight may become blurry or distorted.

Vitelliform macular dystrophy typically does not affect side (peripheral) vision or the ability to see at night.

Two forms of vitelliform macular dystrophy have been described with similar features. The early-onset form (known as Best disease) usually appears in childhood; the onset of symptoms and the severity of vision loss vary widely. The adult-onset form begins later, usually in mid-adulthood, and tends to cause vision loss that worsens slowly over time. The two forms of vitelliform macular dystrophy each have characteristic changes in the macula that can be detected during an eye examination.

In certain embodiments the prophylactic and/or therapeutic methods described herein involve ameliorating one or more of the above symptoms (e.g., one or more symptoms selected from the group consisting of central vision loss, blurry eyesight, distorted eyesight, macular cell death), and/or delaying the onset, slowing, stopping, or reversing the progression of one or more of these symptoms.

Stargardt Disease

Stargardt disease is the most common inherited retinal disease. It usually has an autosomal recessive inheritance caused by mutations in the ABCA4 gene. Rarely it has an autosomal dominant inheritance due to defects with ELOVL4 or PROM1 genes. All forms of Stargardt disease are characterized by macular degeneration as a consequence of lipofuscin accumulation that begins in childhood, adolescence or adulthood, resulting in progressive loss of vision.

Recessive Stargardt disease (STGD1) is an inherited blinding disorder caused by mutations in the Abca4 gene. ABCA4 is a flippase in photoreceptor outer segments (OS) that translocates retinaldehyde conjugated to phosphatidylethanolamine across OS disc membranes. Loss of ABCA4 in Abca4$^{-/-}$ mice and STGD1 patients causes buildup of lipofuscin in the retinal pigment epithelium (RPE) and degeneration of photoreceptors, leading to blindness.

In certain embodiments the prophylactic and/or therapeutic methods described herein involve ameliorating one or more of the above symptoms (e.g., one or more symptoms selected from the group consisting of high levels of vitamin dimers and byproducts thereof, blurry or distorted vision, inability to see in low lighting, difficulty recognizing familiar faces, and loss of color vision), and/or delaying the onset, slowing, stopping, or reversing the progression of one or more of these symptoms.

Neuronal Ceroid Lipofuscinoses

In certain embodiments the molecular tweezers described herein are used in the treatment and/or prophylaxis of a neuronal ceroid lipofuscinosis. Illustrative, but non-limiting examples of neuronal ceroid lipofuscinoses include, but are not limited to, infantile NCL (Santavuori-Haltia disease), late infantile NCL (Jansky-Bielschowsky disease, Juvenile NCL (CLN1, Batten disease), adult NCL (Kufs disease), Finnish Late Infantile NCL, Variant Late Infantile NCL, CLN7 NCL, CLN8 NCL (Northern Epilepsy, progressive epilepsy with mental retardation (EPMR)), Turkish Late Infantile Variant NCL, and CLN10 NCL (Congenital, Cathepsin D Deficiency).

The neuronal ceroid lipofuscinoses (NCLs) are a group of inherited lysosomal storage diseases that together constitute the most common neurodegenerative disorders of childhood. They are clinically and genetically heterogeneous and are characterized by intracellular accumulation of autofluorescent material, neurodegeneration with progressive, permanent loss of motor and psychological ability, and blindness. The stored material, ceroid, shares a similar composition to lipofuscin and is present in most tissues, including brain and retina. Historically, four major NCL subtypes (infantile, late-infantile, juvenile, and adult) have been delineated based on age of onset and the ultrastructure of the storage material. With the advent of molecular genetics, the NCLs have been further classified into eight genetically distinct forms, independent of age of onset (see, e.g., Table 1). All forms of NCL are recessively inherited, with the exception of an adult variant (Parry type).

TABLE 1

Genes known to cause NCL (adapted from Ramirez-Montealegre et al. (2006) Brain, 129(6): 1353-1356).

| Disease | Chromosome Location | Gene Affected | Protein |
| --- | --- | --- | --- |
| Congenital NCL (CNCL) | 11p15.5 | CTSD | Cathepsin D |
| Santavuori-Haltia (INCL) | 1p32 | CLN1 | Palmitoyl protein thioesterase I |
| Jansky-Bielschowsky (LINCL) | 11p15 | CLN2 | Tripeptidyl peptidase protein I |
| Batten, Spielmeyer-Sjogren (JNCL) | 16p12 | CLN3 | Unknown |
| Kufs (ANCL) | Unknown | CLN4* | Unknown |
| Finnish LINCL (vfinLINCL) | 13q31-32 | CLN5 | Unknown |
| Costa Rican LINCL (vLINCL) | 15q21-23 | CLN6 | Unknown |
| Turkish LINCL (vturkLINCL) | 4q28.1-q28.2 | CLN7 (MFSD8) | Unknown |
| Northern Epilepsy/Epilepsy with Progressive Mental Retardation | 8p23 | CLN8 | Unknown |

INCL (infantile neuronal ceroid lipofuscinoses), LINCL (late infantile neuronal ceroid lipofuscinoses), JNCL (juvenile neuronal ceroid lipofuscinoses), CNCL (congenital neuronal ceroid lipofuscinoses), ANCL (adult neuronal ceroid lipofuscinoses).
*Note:
Adult onset NCLs have also been associated to mutations in CLN1

In the early infantile variant of NCL (also called INCL orSantavuori-Haltia), subjects appear normal at birth, but early visual loss leading to complete retinal blindness by the age of 2 years is the first indicator of the disease; by 3 years of age a vegetative state is reached and by 4 years isoelectric encephalograms confirm brain death. Late infantile variant usually manifests between 2 and 4 years of age with seizures and deterioration of vision. The maximum age before death for late infantile variant is 10-12 years. Juvenile NCL (JNCL, Batten Disease, or Spielmeyer-Vogt), JNCL is the most common type of NCL in the United States and Europe with a prevalence of 1 in 100,000, usually arises between 4 and 10 years of age; the first symptoms include considerable vision loss due to retinal dystrophy, with seizures, psychological degeneration. The disease progresses to include seizures, motor deterioration, problems in speech, mental decline, and eventual death in the mid- to late-20s or 30s ensuing. Cardiac problems are also common, especially at late stages of the disease. In advanced disease retinal degeneration is widespread, with neuronal depletion and subsequent atrophy and severe gliosis, similar to that found in advanced retinitis pigmentosa (RP). Adult variant NCL (ANCL or Kuf's Disease) is less understood and generally manifests milder symptoms; however, while symptoms typically appear around 30 years of age, death usually occurs ten years later.

In certain embodiments the prophylactic and/or therapeutic methods described herein involve ameliorating one or more of the above symptoms (e.g., one or more symptoms selected from the group consisting of an amelioration of one or more symptoms selected from the group consisting of cognitive dysfunction, movement/locomotor dysfunction, and vision loss), and/or delaying the onset, slowing, stopping, or reversing the progression of one or more of these symptoms.

The foregoing lipofuscin-related disorders are illustrative and non-limiting. Using the teachings provided herein, one of skill in the art can readily utilize molecular tweezers in the treatment and/or prophylaxis of numerous other lipofuscin-related disorders.

Kits.

In various embodiments kit are provided containing materials for practice of the methods described herein. In certain embodiments the kits comprise a container containing one or more molecular tweezers described herein and/or a pharmaceutical formulation comprising one or more molecular tweezers described herein. In certain embodiments the kits can contain a device (e.g., a pre-loaded syringe) for administering the molecular tweezers In certain embodiments the kits optionally include labeling and/or instructional materials providing directions (e.g., protocols) for the use of the molecular tweezers in the treatment or prophylaxis of a lipofuscin-related disorder, e.g., as described herein. Instructional materials can also include recommended dosages, description(s) of counter indications, and the like.

While the instructional materials in the various kits typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Inhibition of Lipofuscin Aggregation by Molecular Tweezers

To test the effect of CLR01 on lipofuscin aggregation, human, ARPE-19 cells (retinal pigmented epithelium; RPE) were treated with lipofuscin (A2E) in the absence or presence of CLR01 and imaged by fluorescence microscopy at the end of 6 h of incubation (FIG. 1, panel A), as follows:

Condition 1—negative control—20 µl of PBS was added to the cells at t=0 and 20 µl of DMSO at t=1.5 h.

Condition 2—safety control—CLR01 in PBS at final concentration of 100 µM was added to the cells at t=0 and DMSO at t=1.5 h.

Condition 3—positive control—PBS was added to the cells at t=0 and lipofuscin A2E in DMSO at final concentration of 100 µM at t=1.5 h. Lipofuscin A2E is a specific type of lipofuscin enriched in N-retinylidene-N-retinylethanolamine (A2E), which is derived from 11-cis-retinal and accumulates in the retinal pigmented epithelium (Boyer et al. (2012) *J. Biol. Chem.* 287: 22276-22286).

Condition 4—CLR01 in PBS at final concentration of 100 µM was added to the cells at t=0, after 1.5 h, the media was removed, the cells were washed with F12 medium, and new media was added. Lipofuscin A2E in DMSO at final concentration of 100 µM was added at t=1.5 h.

Condition 5—Lipofuscin A2E in DMSO was added to the cells at t=0 and CLR01 in PBS at final concentration of 100 µM was added at t=1 h.

The data showed that CLR01 did not harm the cells (condition 2) and that when CLR01 was added to the cells and washed prior to addition of lipofuscin A2E (condition 4), the fraction of CLR01 that presumably was internalized by the cells was sufficient to reduce the accumulation of lipofuscin aggregates at 6 h by 60%. Moreover, when the cells were incubated first with lipofuscin A2E for 1 h and then exposed to CLR01 (condition 5), the accumulation of lipofuscin aggregates was reduced almost to the negative-control level (FIG. 1, panel B), demonstrating that CLR01 powerfully inhibits the formation of lipofuscin aggregates, presumably by allowing lysosomal degradation of the lipofuscin. Confocal imaging of lipofuscin A2E and lysosomal-associated membrane protein 1 (LAMP-1) showed that lipofuscin colocalized with lysosomes and that the lysosome integrity was not affected by CLR01 (FIG. 1, panel C).

Figure 2:
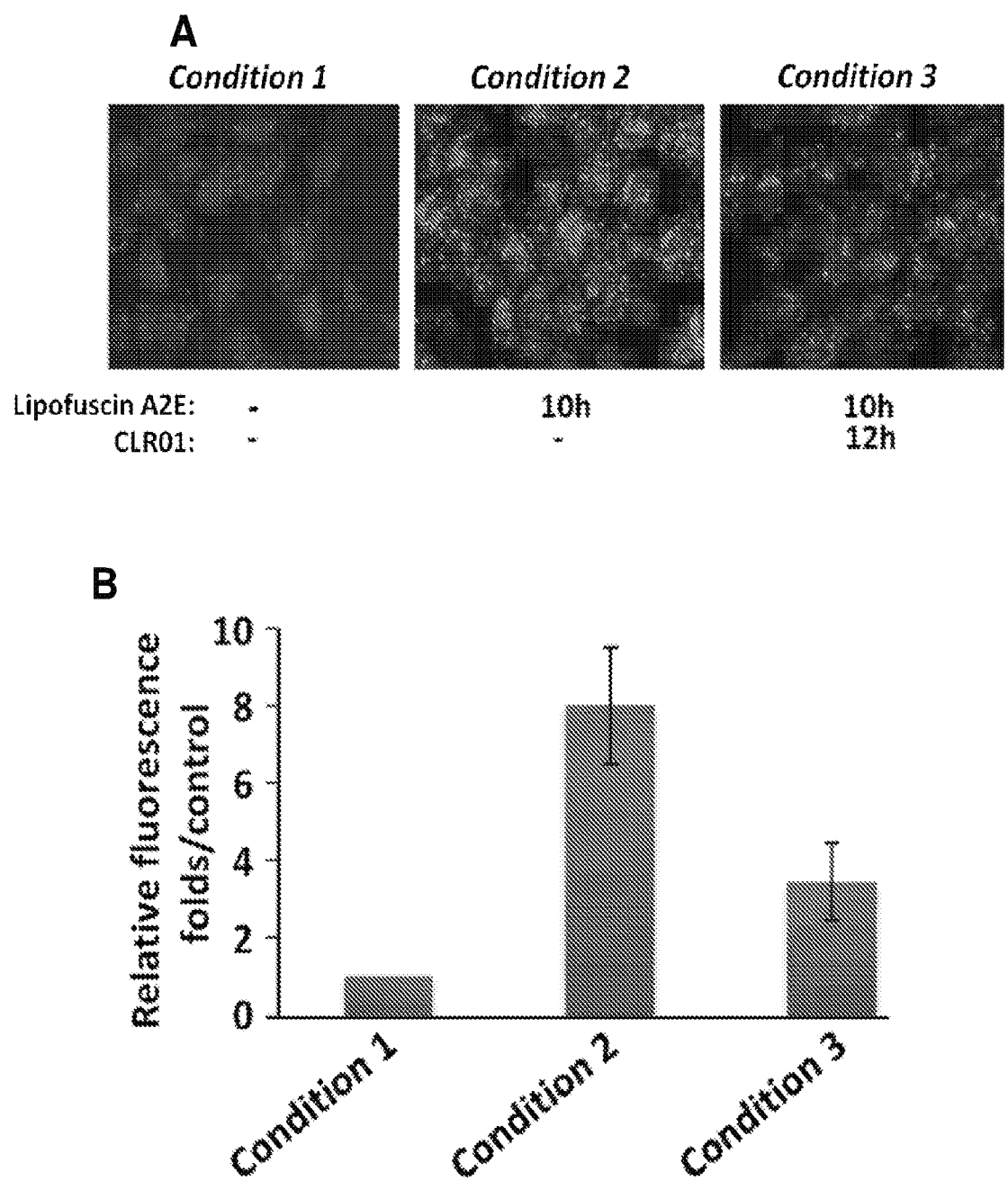
FIG. 2, panel A) CLR01 in PBS and lipofuscin A2E were added to the cells at the indicated times. Cells were incubated up to 22 hours in all cases and were imaged using a fluorescence microscope for visualization of lipofuscin autofluorecence (red) and cell nuclei (DAPI, blue).

The effect of CLR01 on pre-formed lipofuscin aggregates was tested as well. Human, ARPE-19 cells were treated with lipofuscin (A2E) for 10 h (to let lipofuscin aggregates form). Upon washing the cells to remove A2E from the media, CLR01 was added to the medium for an additional period of 12 h. Cells were then imaged by fluorescence microscopy and fluorescence quantified (FIG. 2). The data showed that CLR01 was able to clear lipofuscin in this condition as well. However, its clearing effect was lower respect to the condition in which CLR01 was added simultaneously with lipofuscin loading (condition 5 in FIG. 1).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a lipofuscin-related disorder in a mammal, said method comprising:
   administering to said mammal an effective amount of a molecular tweezers that is capable of inhibiting the accumulation of lipofuscin aggregates;
   wherein said lipofuscin-related disorder is Stargardt disease or a neuronal ceroid lipofuscinosis (NCL); and wherein said molecular tweezers is selected from the group consisting of:

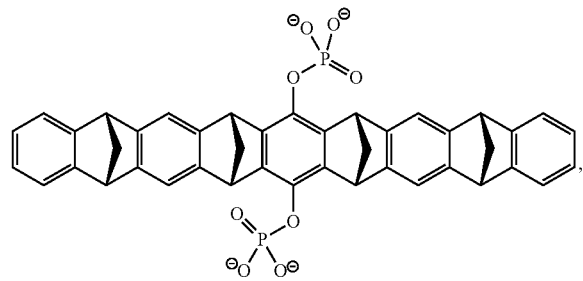 (TW1/CLR01)

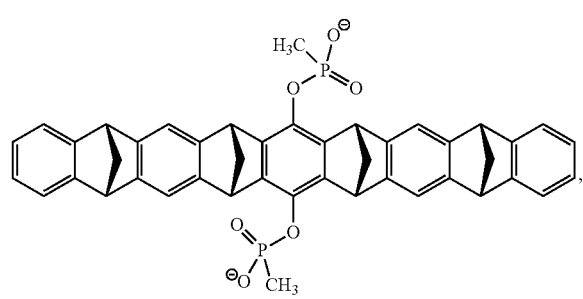 (TW2)

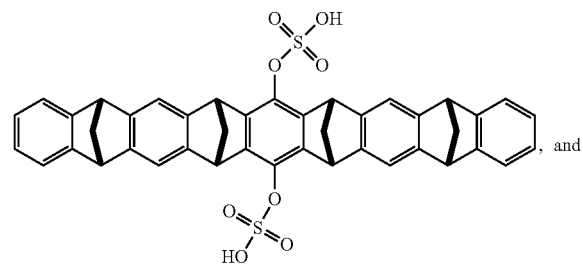 (TW4)

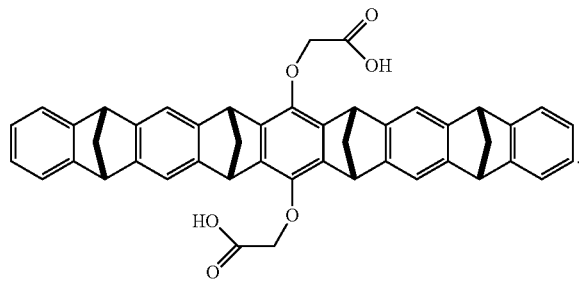 (TW5)

2. The method of claim 1, wherein said molecular tweezers is capable of inhibiting lipofuscin aggregation, and wherein said effective amount is an amount effective to delay the onset of, or to slow the progression, or stop, or to reverse lipofuscin accumulation/aggregation associated with said lipofuscin-related disorder.

3. The method of claim 1, wherein said lipofuscin-related disorder is an NCL, wherein said NCL is selected from the group consisting of infantile NCL (Santavuori-Haltia disease), late Infantile NCL (Jansky-Bielschowsky disease), Juvenile NCL (CLN1, Batten disease), Adult NCL (Kufs disease), Finnish Late Infantile NCL, Variant Late Infantile NCL, CLN7 NCL, CLN8 NCL (Northern Epilepsy, progressive epilepsy with mental retardation (EPMR)), Turkish Late Infantile Variant NCL, and CLN10 NCL (Congenital, Cathepsin D Deficiency).

4. The method of claim 3, wherein said NCL is Batten disease.

* * * * *